United States Patent
Schaub et al.

(10) Patent No.: US 8,426,641 B2
(45) Date of Patent: Apr. 23, 2013

(54) PROCESS FOR PREPARING FORMIC ACID

(75) Inventors: Thomas Schaub, Neustadt (DE); Rocco Paciello, Bad Duerkheim (DE); Klaus-Dieter Mohl, Hockenheim (DE); Daniel Schneider, Mannheim (DE); Martin Schaefer, Gruenstadt (DE); Stefan Rittinger, Mannheim (DE)

(73) Assignee: BASF SE, Ludwigshaden (DE)

( * ) Notice: Subject to any disclaimer, the term of this patent is extended or adjusted under 35 U.S.C. 154(b) by 69 days.

(21) Appl. No.: 12/823,338

(22) Filed: Jun. 25, 2010

(65) Prior Publication Data

US 2010/0331573 A1   Dec. 30, 2010

Related U.S. Application Data

(60) Provisional application No. 61/316,841, filed on Mar. 24, 2010.

(30) Foreign Application Priority Data

Jun. 26, 2009   (EP) ..................................... 09008399

(51) Int. Cl.
*C07C 51/42* (2006.01)
*C07C 53/00* (2006.01)

(52) U.S. Cl.
USPC .......................................... 562/609; 562/608

(58) Field of Classification Search .......................... None
See application file for complete search history.

(56) References Cited

U.S. PATENT DOCUMENTS

| | | | |
|---|---|---|---|
| 5,294,740 A | 3/1994 | Kiefer et al. | |
| 7,420,088 B2 * | 9/2008 | Karl et al. | 562/609 |
| 2010/0063320 A1 | 3/2010 | Challand et al. | |

FOREIGN PATENT DOCUMENTS

| | | |
|---|---|---|
| DE | 3428319 A1 | 2/1986 |
| DE | 4431233 A1 | 3/1995 |
| EP | 0 001 432 A1 | 4/1979 |
| EP | 0095321 * | 11/1983 |
| EP | 0095321 A2 | 11/1983 |
| EP | 0126524 A1 | 11/1984 |
| EP | 0151510 A1 | 8/1985 |
| EP | 0181078 * | 5/1986 |

(Continued)

OTHER PUBLICATIONS

Wagner, "Reaktionen mit aktivierte Ameisensaeure enthaltenden Additionsverbindungen", *Angew. Chem.*, vol. 82, No. 2, pp. 73-77 (1970).

(Continued)

*Primary Examiner* — Karl J Puttlitz
(74) *Attorney, Agent, or Firm* — Novak Druce Connolly Bove + Quigg LLP

(57) ABSTRACT

Process for preparing formic acid by hydrogenation of carbon dioxide in the presence of a catalyst comprising an element of group 8, 9 or 10 of the Periodic Table, a tertiary amine and a polar solvent at a pressure of from 0.2 to 30 MPa abs and a temperature of from 20 to 200° C. to form two liquid phases, separation of the two liquid phases, wherein the liquid phase (B) enriched with the tertiary amine is recirculated to the hydrogenation reactor and the formic acid/amine adduct from the liquid phase (A) enriched with the formic acid/amine adduct and the polar solvent is thermally dissociated into free formic acid and free tertiary amine in a distillation unit and the tertiary amine liberated in the dissociation and the polar solvent are recirculated to the hydrogenation reactor.

11 Claims, 3 Drawing Sheets

| | FOREIGN PATENT DOCUMENTS | | |
|----|----|----|----|
| EP | 0181078 A1 | 5/1986 |
| EP | 0329337 A2 | 8/1989 |
| EP | 0357243 A2 | 3/1990 |
| EP | 0563831 A2 | 10/1993 |
| EP | 1053219 A1 | 11/2000 |
| EP | 1265832 A2 | 12/2002 |
| GB | 1028930 A | 5/1966 |
| WO | WO-2006/021411 A1 | 3/2006 |
| WO | WO-2008/116799 A1 | 10/2008 |

OTHER PUBLICATIONS

Leitner, "Kohlendioxid als Rohstoff am Beispiel der Synthese von Ameisensaeure und ihren Derivaten", *Angew. Chem.*, vol. 107, pp. 2391-2405 (1995).

Jessop et al., "Homogeneous Hydrogenation of Carbon Dioxide", *American Chemical Reviews*, vol. 95, No. 2, pp. 259-272 (1995).

* cited by examiner

US 8,426,641 B2

PROCESS FOR PREPARING FORMIC ACID

RELATED APPLICATIONS

This application claims benefit of European Application No. 09008399.9, filed Jun. 26, 2009, and U.S. Provisional Application Ser. No. 61/316,841, filed Mar. 24, 2010, which is incorporated by reference herein in its entirety.

The present invention relates to a process for preparing formic acid by hydrogenation of carbon dioxide in the presence of a catalyst comprising an element of group 8, 9 or 10 of the Periodic Table, a tertiary amine (I) and a polar solvent (III) at a pressure of from 0.2 to 30 MPa abs and a temperature of from 20 to 200° C. to form two liquid phases, separation of the one liquid phase (A) enriched with the formic acid/amine adduct (II) from the other liquid phase (B) and recirculation of the liquid phase (B) to the hydrogenation reactor.

Adducts of formic acid and tertiary amines can be thermally dissociated into free formic acid and tertiary amine and therefore serve as intermediate in the preparation of formic acid. Formic acid is an important and versatile product. It is used, for example, for acidification in the production of animal feeds, as preservative, as disinfectant, as auxiliary in the textile and leather industry, as a mixture with its salts for deicing aircraft and runways and also as synthetic building block in the chemical industry.

The abovementioned adducts of formic acid and tertiary amines can be prepared in various ways, for example (i) by direct reaction of tertiary amine with formic acid, (ii) by hydrolysis of methyl formate to form formic acid in the presence of the tertiary amine or with subsequent extraction of the hydrolysis product with the tertiary amine or (iii) by catalytic hydration of carbon monoxide or hydrogenation of carbon dioxide to form formic acid in the presence of the tertiary amine. The latter process of catalytic hydrogenation of carbon dioxide has the particular attraction that carbon dioxide is available in large quantities and is flexible in terms of source.

WO 2008/116,799 discloses a process for the hydrogenation of carbon dioxide in the presence of a catalyst which comprises a transition metal of transition group VIII (groups 8, 9, 10) and is suspended or homogeneously dissolved in a solution, a tertiary amine having at least one hydroxyl group and a polar solvent to form an adduct of formic acid and the tertiary amine. The hydroxyl group(s) in the tertiary amine enable an increased carbon dioxide solubility compared to the triethylamine which is usually used to be achieved. As preferred homogeneous catalysts, mention may be made of $RuH_2L_4$ having monodentate phosphorus-based ligands L and $RuH_2(LL)_2$ having bidentate phosphorus-based ligands LL and particularly preferably $RuH_2[P(C_6H_5)_3]_4$. As polar solvents, mention may be made of alcohols, ethers, sulfolanes, dimethyl sulfoxide and amides whose boiling point at atmospheric pressure is at least 5° C. above that of formic acid. The tertiary amines which are preferably to be used also have a boiling point above that of formic acid. Since no phase separation takes place, the work-up of the entire reaction product mixture is carried out by distillation, if appropriate after prior removal of the catalyst, in which the adduct of formic acid and the tertiary amine which is formed is thermally dissociated and the formic acid liberated is isolated as overhead product. The bottom product comprising tertiary amine, polar solvent and, if appropriate, catalyst is recirculated to the hydrogenation stage.

A disadvantage of this process is the introduction of the entire liquid reaction product mixture into the apparatus for thermal dissociation and distillation, if appropriate after prior specific removal of the homogeneous catalyst by means of a separate process step, for example an extraction, adsorption or ultrafiltration step. The apparatus for the thermal dissociation and distillation consequently has to be made larger and more complex both in terms of the higher liquid throughput and the more specific separation properties, which is reflected, inter alia, in the capital costs (for example via engineering input, material, space requirement). In addition, the higher liquid throughput also results in a higher energy usage.

However, the fundamental work on the catalytic hydrogenation of carbon dioxide to form formic acid was carried out as early as the 1970s and 1980s. The processes of BP Chemicals Ltd. filed as the patents EP 0 095 321 A, EP 0 151 510 A and EP 0 181 078 A may be considered to result therefrom. All three documents describe the hydrogenation of carbon dioxide in the presence of a homogeneous catalyst comprising a transition metal of transition group VIII (groups 8, 9, 10), a tertiary amine and a polar solvent to form an adduct of formic acid and the tertiary amine. As preferred homogeneous catalysts, EP 0 095 321 A and EP 0 181 078 A in each case make mention of ruthenium-based carbonyl-, halide- and/or triphenylphosphine-comprising complex catalysts and EP 0 151 510 A mentions rhodium-phosphine complexes. Preferred tertiary amines are $C_1$-$C_{10}$-trialkylamines, in particular the short-chain $C_1$-$C_4$-trialkylamines, and also cyclic and/or bridged amines such as 1,8-diazabicyclo[5.4.0]undec-7-ene, 1,4-diazabicyclo[2.2.2]octane, pyridine or picolines. The hydrogenation is carried out at a carbon dioxide partial pressure of up to 6 MPa (60 bar), a hydrogen partial pressure of up to 25 MPa (250 bar) and a temperature from about room temperature to 200° C.

EP 0 095 321 A and EP 0 151 510 A teach the use of an alcohol as polar solvent. However, since primary alcohols tend to form formic esters (organic formates), secondary alcohols, in particular isopropanol, are preferred. In addition, the presence of water is described as advantageous. According to the examples in EP 0 095 321 A, the reaction product mixture is worked up by directly subsequent two-stage distillation in which the low boilers alcohol, water, tertiary amine are separated off in the first stage and the adduct of formic acid and the tertiary amine is separated off at the top under vacuum conditions in the second stage. EP 0 151 510 A likewise teaches a work-up by distillation, but with reference to EP 0 126 524 A with subsequent replacement of the tertiary amine in the adduct which has been separated off by distillation by a weaker, less volatile nitrogen base before thermal cleavage of the adduct in order to aid or make possible the subsequent thermal dissociation to produce free formic acid.

EP 0 181 078 A teaches the targeted choice of the polar solvent on the basis of three essential criteria which have to be fulfilled at the same time:
(i) the homogeneous catalyst has to be soluble in the polar solvent;
(ii) the polar solvent must not have an adverse effect on the hydrogenation; and
(iii) the adduct of formic acid and the tertiary amine which is formed should be able to be readily separated off from the polar solvent.

As particularly suitable polar solvents, mention is made of various glycols and phenylpropanols.

According to the teaching of EP 0 181 078 A, the work-up of the reaction product mixture is carried out by firstly separating off the gaseous components (in particular unreacted starting materials hydrogen and carbon dioxide) at the top of an evaporator and separating off the homogeneous catalyst dissolved in the polar solvent at the bottom and recirculating them to the hydrogenation stage. The adduct of formic acid and the tertiary amine is subsequently separated off from the remaining liquid phase comprising the adduct of formic acid and the tertiary amine, free tertiary amine and possibly water and the remaining part of the liquid phase comprising the free tertiary amine and possibly water is recirculated to the hydrogenation stage. The separation can be effected by distillation or phase separation of the two-phase system (decantation).

A further significant teaching of EP 0 181 078 A is the subsequent, absolutely necessary replacement of the tertiary amine in the adduct which has been separated off by a weaker, less volatile nitrogen base before the adduct is thermally dissociated in order to aid or make possible the subsequent thermal dissociation to produce free formic acid. As particularly suitable weaker nitrogen bases, mention is made of imidazole derivatives such as 1-n-butylimidazole.

A disadvantage of the process of EP 0 181 078 A is the very complicated, four-stage work-up of the reaction product mixture by
  (i) separating off the gaseous components and also the homogeneous catalyst and the polar solvent in an evaporator and recirculating them to the hydrogenation stage;
  (ii) separating off the adduct of formic acid and the tertiary amine in a distillation column or a phase separator and recirculating the remaining liquid stream to the hydrogenation stage;
  (iii) replacing the tertiary amine in the adduct of formic acid and the tertiary amine by a weaker, less volatile nitrogen base in a reaction vessel having a superposed distillation column and recirculating the tertiary amine liberated to the hydrogenation stage; and
  (iv) thermally dissociating the adduct of formic acid and the weaker nitrogen base and recirculating the weaker nitrogen base liberated to the base replacement stage.

A further, important disadvantage of the process of EP 0 181 078 A and also of the processes of EP 0 095 321 A and EP 0 151 510 A is the fact that the adduct of formic acid and the tertiary amine partly redissociates into carbon dioxide and hydrogen in the presence of the homogeneous catalyst during the work-up in the evaporator. As a solution to this problem, EP 0 329 337 A proposes the addition of a decomposition inhibitor which reversibly inhibits the homogeneous catalyst. As preferred decomposition inhibitors, mention is made of carbon monoxide and oxidants. However, disadvantages of this are the introduction of further substances into the overall process and the necessity of reactivating the inhibited homogeneous catalyst before it is used further.

EP 0 357 243 A, too, addresses the disadvantage of the partial redissociation of the adduct of formic acid and the tertiary amine in the process of EP 0 181 078 A by joint work-up of the reaction product mixture in the evaporator. The process proposed in EP 0 357 243 A teaches the use of a homogeneous catalyst comprising a transition metal of transition group VIII (groups 8, 9, 10), a tertiary amine and two different solvents, namely a nonpolar, inert solvent and a polar, inert solvent, which form two immiscible liquid phases in the catalytic hydrogenation of carbon dioxide to form an adduct of formic acid and tertiary amine. As nonpolar solvents, mention is made of aliphatic and aromatic hydrocarbons but also of phosphines having aliphatic and/or aromatic hydrocarbon radicals. Polar solvents mentioned are water, glycerol, alcohols, polyols, sulfolanes and mixtures thereof, with water being preferred. The homogeneous catalyst dissolves in the nonpolar solvent and the adduct of formic acid and tertiary amine dissolves in the polar solvent. After the reaction is complete, the two liquid phases are separated, for example by decantation, and the nonpolar phase comprising the homogeneous catalyst and the nonpolar solvent is recirculated to the hydrogenation stage. The polar phase comprising the adduct of formic acid and tertiary amine and the polar solvent is then subjected to an absolutely necessary replacement of the tertiary amine in the adduct by a weaker, less volatile nitrogen base before thermal dissociation of the adduct in order to aid or make possible the subsequent thermal dissociation to produce free formic acid. In a manner analogous to EP 0 181 078 A, imidazole derivatives such as 1-n-butylimidazole are also mentioned here as particularly suitable weaker nitrogen bases.

A disadvantage of the process of EP 0 357 243 A is the very complicated, three-stage work-up of the reaction product mixture by
  (i) separating the two liquid phases and recirculating the phase comprising the homogeneous catalyst and the nonpolar solvent to the hydrogenation stage;
  (ii) replacing the tertiary amine in the adduct of formic acid and the tertiary amine of the other phase by a weaker, less volatile nitrogen base in a reaction vessel with superposed distillation column and recirculating the tertiary amine liberated to the hydrogenation stage; and
  (iii) thermally dissociating the adduct of formic acid and the weaker nitrogen base and recirculating the weaker nitrogen base liberated to the base replacement stage.

A further disadvantage of the process of EP 0 357 243 A is the use of two solvents and thus introduction of a further substance into the overall process.

As an alternative, EP 0 357 243 A also discloses the possibility of using only one solvent. In this case, the addition of the polar solvent in which the adduct of formic acid and the tertiary amine would otherwise dissolve is omitted. The sole solvent used here is the nonpolar solvent which dissolves the homogeneous catalyst. However, this alternative also has the disadvantage of the very complicated, three-stage work-up as described above.

DE 44 31 233 A likewise describes the hydrogenation of carbon dioxide in the presence of a catalyst comprising a transition metal of transition group VIII (groups 8, 9, 10), a tertiary amine and a polar solvent and water to form an adduct of formic acid and the tertiary amine, in which, however, the catalyst is present in heterogeneous form and the active component is applied to a inert support. Preferred tertiary amines are $C_1$-$C_8$-trialkylamines, polyamines having from 2 to 5 amino groups, aromatic nitrogen heterocycles such as pyridine or N-methylimidazole and also cyclic and/or bridged amines such as N-methylpiperidine, 1,8-diazabicyclo[5.4.0]undec-7-ene or 1,4-diazabicyclo[2.2.2]octane. As suitable polar solvents, mention is made of the low-boiling $C_1$-$C_4$-monoalcohols, and, in a manner analogous to EP 0 095 321 A, secondary alcohols are preferred. The hydrogenation is carried out at a total pressure of from 4 to 20 MPa (from 40 to 200 bar) and a temperature of from 50 to 200° C. For the work-up of the adduct of formic acid and tertiary amine which is formed, DE 44 31 233 A teaches the use of known methods with explicit reference to the work-up with replacement of the tertiary amine in the adduct of formic acid and the tertiary amine by a weaker, less volatile nitrogen base as disclosed in EP 0 357 243 A. In a manner analogous to the process of EP 0 357 243 A, the process of DE 44 31 233 A also has the disadvantage of the very complicated, three-stage work-up of the reaction product mixture.

It was an object of the present invention to discover a process for preparing formic acid by hydrogenation of carbon dioxide, which does not have the abovementioned disadvantages of the prior art or suffers from them only to a significantly reduced extent and allows concentrated formic acid to be obtained in a high yield and high purity. Furthermore, the process should be able to be carried out in a simple manner or at least a simpler manner than is described in the prior art, for example by means of a different, simpler process concept, simpler process stages, a reduced number of process stages or simpler apparatuses. In addition, the process should also be able to be carried out with a reduced consumption of energy.

Figure 1:
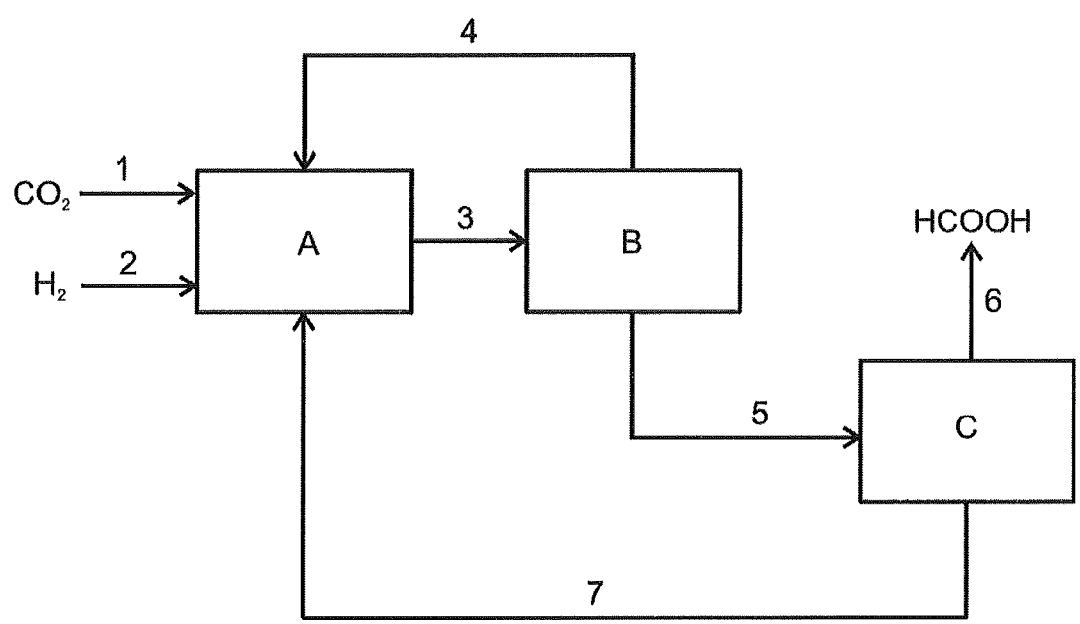
FIG. 1 depicts a schematic block diagram of a possible embodiment of the process of the invention.

We have accordingly found a process for preparing formic acid by hydrogenation of carbon dioxide in the presence of a catalyst comprising an element of group 8, 9 or 10 of the Periodic Table, a tertiary amine (I) and a polar solvent (III) at a pressure of from 0.2 to 30 MPa abs and a temperature of from 20 to 200° C. to form two liquid phases, separation of the one liquid phase (A) enriched with the formic acid/amine adduct (II) from the other liquid phase (B) and recirculation of the liquid phase (B) to the hydrogenation reactor, wherein
  (a) an amine which at a pressure of 1013 hPa abs has a boiling point which is at least 5° C. higher than that of formic acid and is present in enriched form in the liquid phase (B) is used as tertiary amine (I);
  (b) a solvent whose electrostatic factor is $\geqq 200 \cdot 10^{-30}$ Cm and which at a pressure of 1013 hPa abs has a boiling point which is at least 5° C. higher than that of formic acid and is present in enriched form in the liquid phase (A) is used as polar solvent (III);
  (c) the formic acid/amine adduct (II) of the liquid phase (A) which has been separated off is thermally dissociated into free formic acid and free tertiary amine (I) in a distillation unit;
  (d) the free formic acid is removed by distillation; and
  (e) the free tertiary amine (I) comprised in the bottoms from the distillation unit and the polar solvent (III) are recirculated to the hydrogenation reactor.

The catalyst to be used in the hydrogenation of carbon dioxide in the process of the invention can be heterogeneous or homogeneous in nature. It comprises an element of group 8, 9 or 10 of the Periodic Table, i.e. Fe, Co, Ni, Ru, Rh, Pd, Os, Ir and/or Pt. The catalyst preferably comprises Ru, Rh, Pd, Os, Ir and/or Pt, particularly preferably Ru, Rh and/or Pd, very particularly preferably Ru. The catalytically active components can be the metals themselves, for example in finely divided form, or complexes.

In the case of a heterogeneous catalyst, the elements mentioned are preferably present as metals on an inert support. Inert support materials can be, for example, silicon dioxide, aluminum oxide, zirconium oxide or mixtures of these oxides and also graphite. As particularly preferred heterogeneous catalysts, mention may be made of Ru/aluminum oxide, Pd/graphite and triphenylphosphine complexes of Rh or Ru, for example bis(triphenylphosphine)ruthenium dichloride or tris(triphenylphosphine)rhodium chloride, on silicon dioxide. The content of the elements mentioned is generally from 0.1 to 10% by weight, based on the heterogeneous catalyst. The heterogeneous catalysts can be used in various geometric shapes and sizes. In the case of a fixed-bed catalyst, use is made of, for example, pellets, cylinders, hollow cylinders, spheres, rods or extrudates. Their average particle diameter is generally from 2 to 5 mm. When heterogeneous catalysts are used, the amount of the abovementioned metal component used is generally from 0.01 to 100% by weight, based on the total weight of the catalyst, with all-active catalysts, for example Raney nickel or nanopalladium, being able to comprise up to 100% by weight of the respective metal. Suitable heterogeneous catalysts are commercially available or can be obtained by treatment of the support with solutions of the metal components and subsequent drying, heat treatment and/or calcination by known methods.

If a heterogeneous catalyst is used in the process of the invention, this preferably remains in the hydrogenation reactor. This is made possible, for example, by it being present in the form of a fixed-bed catalyst fixed in position in the reactor or in the case of a suspended catalyst being retained in the reactor by means of a suitable screen or a suitable filter.

In the case of a homogeneous catalyst, the abovementioned elements are homogeneously dissolved in the form of complex-like compounds in the reaction mixture. The homogeneous catalyst should be selected so that it is present in enriched form together with the tertiary amine (I) in the liquid phase (B). For the present purposes, "in enriched form" means a partition coefficient of the homogeneous catalyst $P$=[concentration of homogeneous catalyst in liquid phase $(B)$]/[concentration of homogeneous catalyst in liquid phase $(A)$]

of >1. The partition coefficient is preferably 10 and particularly preferably $\geqq 20$. The choice of the homogeneous catalyst is generally made by means of a simple test in which the partition coefficient of the desired homogeneous catalyst under the planned process conditions is determined experimentally.

Owing to their good solubility in tertiary amines (I), preference is given to using metal-organic complexes comprising an element of group 8, 9 or 10 of the Periodic Table and at least one phosphine group having at least one unbranched or branched, acyclic or cyclic, aliphatic radical having from 1 to 12 carbon atoms, where individual carbon atoms can also be substituted by >P—, as homogeneous catalysts in the process of the invention. Branched cyclic aliphatic radicals thus also include radicals such as —$CH_2$—$C_6H_{11}$. Suitable radicals are, for example, methyl, ethyl, 1-propyl, 2-propyl, 1-butyl, 2-butyl, 1-(2-methyl)propyl, 2-(2-methyl)propyl, 1-pentyl, 1-hexyl, 1-heptyl, 1-octyl, 1-nonyl, 1-decyl, 1-undecyl, 1-dodecyl, cyclopentyl, cyclohexyl, cycloheptyl and cyclooctyl, methylcyclopentyl, methylcyclohexyl, 1-(2-methyl)pentyl 1-(2-ethyl)hexyl, 1-(2-propyl)heptyl and norbornyl. The unbranched or branched, acyclic or cyclic, aliphatic radical preferably comprises at least 1 and preferably not more than 10 carbon atoms. In the case of an exclusively cyclic radical in the abovementioned sense, the number of carbon atoms is from 3 to 12 and preferably at least 4 and also preferably not more than 8. Preferred radicals are 1-butyl, 1-octyl and cyclohexyl.

The phosphine group can comprise one, two or three of the above-mentioned unbranched or branched, acyclic or cyclic, aliphatic radicals. These can be identical or different. The phosphine group preferably comprises three of the above-mentioned unbranched or branched, acyclic or cyclic, aliphatic radicals and particular preference is given to all three radicals being identical. Preferred phosphines are P(n-$C_nH_{2n+1}$)$_3$ where n is from 1 to 10, particularly preferably tri-n-butylphosphine, tri-n-octylphosphine, very particularly preferably tri-n-butylphosphine and tri-n-octylphosphine and in particular tri-n-butylphosphine.

As mentioned above, individual carbon atoms can also be substituted by >P— in the abovementioned unbranched or branched, acyclic or cyclic, aliphatic radicals. Polydentate, for example bidentate or tridentate, phosphine ligands are thus also comprised. These preferably comprise the group

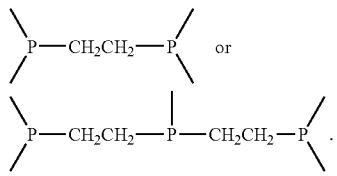

If the phosphine group comprises radicals other than the above-mentioned unbranched or branched, acyclic or cyclic, aliphatic radicals, these generally correspond to those which are otherwise customarily used in phosphine ligands for metal-organic complex catalysts. Examples which may be mentioned are phenyl, tolyl and xylyl.

The metal-organic complex can comprise one or more, for example two, three or four, of the abovementioned phosphine groups having at least one unbranched or branched, acyclic or cyclic, aliphatic radical. The remaining ligands of the metal-organic complex can have various natures. Examples which may be mentioned are hydride, fluoride, chloride, bromide, iodide, formate, acetate, propionate, carboxylates, acetylacetonate, carbonyl, dimethyl sulfoxide, hydroxide, trialkylamine, alkoxides.

The homogeneous catalysts can either be used directly in their active form or be generated only under reaction conditions from customary standard complexes such as [M(p-cymene)Cl$_2$]$_2$, [M(benzene)Cl$_2$]$_n$, [M(COD)(allyl)], [MCl$_3$×H$_2$O], [M(acetylacetonate)$_3$], [M(DMSO)$_4$Cl$_2$] where M is an element of group 8, 9 or 10 of the Periodic Table by addition of the corresponding phosphine ligand or ligands.

Homogeneous catalysts which are preferred in the process of the invention are [Ru(P″Bu$_3$)$_4$(H)$_2$], [Ru(P″octyl$_3$)$_4$(H)$_2$], [Ru(P″Bu$_3$)$_2$(1,2-bis(dicyclohexylphosphino)ethane)(H)$_2$], [Ru(P″octyl$_3$)$_2$(1,2-bis(dicyclohexylphosphino)ethane)(H)$_2$]. By means of these, TOF (turnover frequency) values of greater than 1000 h$^{-1}$ can be achieved in the hydrogenation of carbon dioxide.

When homogeneous catalysts are used, the amount of the specified metal component in the metal-organic complex which is used is generally from 0.1 to 5000 ppm by weight, preferably from 1 to 800 ppm by weight and particularly preferably from 5 to 500 ppm by weight, in each case based on the total liquid reaction mixture in the hydrogenation reactor.

In the process of the invention, preference is given to using a homogeneous catalyst as catalyst in the hydrogenation of carbon dioxide.

When a homogeneous catalyst is used, this is also present in enriched form in the liquid phase (B) and can thus be largely recirculated to the hydrogenation reactor via the liquid phase (B); thus, the liquid phase (A) enriched in the formic acid/amine adduct (II) generally still comprises valuable residual amounts of catalyst. These can lead to a backreaction with decomposition into carbon dioxide and hydrogen in the thermal dissociation, which equates to a decrease in the yield of formic acid. In addition, the homogeneous catalyst carried through the thermal dissociation can generally not be used in the hydrogenation step without renewed activation or work-up. It is therefore preferred, in the process of the invention, that in feature (e) the bottoms from the distillation unit are separated into a phase comprising the free tertiary amine (I) and a phase comprising the polar solvent (III) and the two phases are separately recirculated to the hydrogenation reactor, with the phase comprising the free tertiary amine (I) being recirculated via an extraction unit to the hydrogenation reactor and, in said extraction unit, extracting homogeneous catalyst from the liquid phase (A) which has been separated off, before the formic acid/amine adduct (II) in the liquid phase (A) which has been separated off is, according to feature (c), thermally dissociated into free formic acid and free tertiary amine (I) in a distillation unit.

The extraction is generally carried out at a temperature of from 0 to 150° C. and a pressure of from 0.1 to 8.0 MPa abs. The temperature is preferably at least 20° C. and particularly preferably at least 30° C. and also preferably not more than 100° C. and particularly preferably not more than 80° C. The pressure is preferably at least 0.01 MPa abs. and particularly preferably at least 0.1 MPa abs. and also preferably not more than 10 MPa abs. and particularly preferably not more than 1 MPa abs.

The extraction unit comprises both a facility for extraction and a facility for separating the two liquid phases. The two parts can be integrated together in one apparatus or be divided over a plurality of apparatuses. In principle, the extraction mentioned can be carried out in any suitable apparatus known to those skilled in the art. Preference is given to using a countercurrent extraction column, a mixer-settler cascade or a combination of mixer-settlers with columns.

The additional extraction step is particularly advantageously used when the liquid phase (A) enriched in the formic acid/amine adduct (II) still comprises more than 10 ppm by weight of catalyst metal. However, it is also advisable to use the additional extraction step even when more than 1 ppm by weight of catalyst metal is present in the liquid phase (A).

It can be advantageous to integrate an apparatus for the adsorption of traces of the homogeneous catalyst into the apparatus between the extraction unit and the distillation unit in which the thermal dissociation occurs. Suitable adsorbents are known to those skilled in the art. Examples of suitable adsorbents are, for example, polyacrylic acid and salts thereof, sulfonated polystyrenes and salts thereof, activated carbons, montmorillonites, bentonites, silica gels and zeolites.

The tertiary amine (I) to be used in the hydrogenation of carbon dioxide in the process of the invention has a boiling point which is at least 5° C. higher than that of formic acid at a pressure of 1013 hPa abs. The tertiary amine (I) is to be selected or matched to the polar solvent (III) so that the tertiary amine (I) is present in enriched form in the liquid phase (B). For the present purposes, "in enriched form" means a proportion by weight of >50% of the free, i.e. not bound in the form of the formic acid/amine adduct (II), tertiary amine (I) in the liquid phase (B), based on the total amount of free, tertiary amine (I) in the two liquid phases (A) and (B). The proportion by weight is preferably >90%, particularly preferably >95% and very particularly preferably >97%. The tertiary amine (I) is generally selected by means of a simple test in which the solubility of the desired tertiary amine (I) in the two liquid phases (A) and (B) under the planned process conditions is determined experimentally.

The tertiary amine (I) to be used preferably has a boiling point which is at least 10° C. higher, particularly preferably at least 50° C. higher and very particularly preferably at least 100° C. higher, than that of formic acid. A restriction in terms of an upper limit to the boiling point is not necessary since a very low vapor pressure of the tertiary amine (I) is in principle an advantage for the process of the invention. In general, the boiling point of the tertiary amine (I) at a pressure of 1013 hPa abs, if necessary at a pressure extrapolated by known methods from vacuum to 1013 hPa abs, is below 500° C.

The tertiary amine (I) which is preferably to be used in the process of the invention is an amine of the general formula (Ia)

$$NR^1R^2R^3 \quad (Ia)$$

where the radicals $R^1$ to $R^3$ are identical or different and are each, independently of one another, an unbranched or branched, acyclic or cyclic, aliphatic, araliphatic or aromatic radical having in each case from 1 to 16 carbon atoms, preferably from 1 to 12 carbon atoms, where individual carbon atoms can also be substituted, independently of one another, by a hetero group selected from the group consisting of —O— and >N— or two or all three radicals can also be joined to one another to form a chain comprising at least four atoms in each case.

Examples of Suitable Amines are:
Tri-n-propylamine (bp$_{1013\ hPa}$=156° C.), tri-n-butylamine, tri-n-pentylamine, tri-n-hexylamine, tri-n-heptylamine, tri-n-octylamine, tri-n-nonylamine, tri-n-decylamine, tri-n-undecylamine, tri-n-dodecylamine, tri-n-tridecylamine, tri-n-tetradecylamine, tri-n-pentadecylamine, tri-n-hexadecylamine, tri(2-ethylhexyl)amine.
Dimethyldecylamine, dimethyldodecylamine, dimethyltetradecylamine, ethyldi(2-propyl)amine (bp$_{1013\ hPa}$=127° C.), dioctylmethylamine, dihexylmethylamine.
Tricyclopentylamine, tricyclohexylamine, tricycloheptylamine, tricyclooctylamine and derivatives thereof which are substituted by one or more methyl, ethyl, 1-propyl, 2-propyl, 1-butyl, 2-butyl or 2-methyl-2-propyl groups.
Dimethylcyclohexylamine, methyldicyclohexylamine, diethylcyclohexylamine, ethyldicyclohexylamine, dimethylcyclopentylamine, methyldicyclopentylamine.
Triphenylamine, methyldiphenylamine, ethyldiphenylamine, propyldiphenylamine, butyldiphenylamine, 2-ethylhexyldiphenylamine, dimethylphenylamine, diethylphenylamine, dipropylphenylamine, dibutylphenylamine, bis(2-ethylhexyl)phenylamine, tribenzylamine, methyldibenzylamine, ethyldibenzylamine and derivatives thereof which are substituted by one or more methyl, ethyl, 1-propyl, 2-propyl, 1-butyl, 2-butyl or 2-methyl-2-propyl groups.
N—C$_1$-C$_{12}$-alkylpiperidines, N,N-di-C$_1$-C$_{12}$-alkylpiperazines, N—C$_1$-C$_{12}$-alkylpyrrolidines, N—C$_1$-C$_{12}$-alkylimidazoles and derivatives thereof which are substituted by one or more methyl, ethyl, 1-propyl, 2-propyl, 1-butyl, 2-butyl or 2-methyl-2-propyl groups.
1,8-Diazabicyclo[5.4.0]undec-7-ene ("DBU"), 1,4-diazabicyclo[2.2.2]octane ("DABCO"), N-methyl-8-azabicyclo[3.2.1]octane ("tropane"), N-methyl-9-azabicyclo[3.3.1]nonane ("granatane"), 1-azabicyclo[2.2.2]octane ("quinuclidine").

It is naturally also possible to use mixtures of various tertiary amines (I) in the process of the invention.

Among the above-described tertiary amines of the general formula (Ia), preference is given to those in which the radicals $R^1$ to $R^3$ are identical or different and are each, independently of one another, an unbranched or branched, acyclic or cyclic, aliphatic, araliphatic or aromatic radical having in each case from 1 to 16 carbon atoms, preferably from 1 to 12 carbon atoms, where individual carbon atoms can, independently of one another, also be substituted by a hetero group selected from the group consisting of —O— and >N— or two or all three radicals can also be joined to one another to form a saturated chain comprising at least four atoms in each case.

Preference is given to at least one of the radicals bearing two hydrogen atoms on the alpha-carbon atom.

In the process of the invention, particular preference is given to using an amine of the general formula (Ia) in which the radicals $R^1$ to $R^3$ are selected independently from the group consisting of C$_1$-C$_{12}$-alkyl, C$_5$-C$_8$-cycloalkyl, benzyl and phenyl as tertiary amine (I).

Particular preference is given to using a saturated amine of the general formula (Ia) as tertiary amine (I) in the process of the invention.

Very particular preference is given to using an amine of the general formula (Ia) in which the radicals $R^1$ to $R^3$ are selected independently from the group consisting of C$_5$-C$_8$-alkyl, in particular tri-n-pentylamine, tri-n-hexylamine, tri-n-heptylamine, tri-n-octylamine, dimethylcyclohexylamine, methyldicyclohexylamine, dioctylmethylamine and dimethyldecylamine, as tertiary amine (I) in the process of the invention.

The tertiary amine (I) is preferably present in liquid form in all process stages of the process of the invention. However, this is not absolutely necessary. It would also be sufficient for the tertiary amine (I) to be at least dissolved in suitable solvents. Suitable solvents are in principle those which are chemically inert in respect of the hydrogenation of carbon dioxide and the thermal dissociation of the adduct and in which the tertiary amine (I) and, if a homogeneous catalyst is used, also the latter readily dissolve but do not readily dissolve the polar solvent (III) and the formic acid/amine adduct (II) and at a pressure of 1013 hPa abs have a boiling point which is at least 5° C. higher than that of formic acid. Possibilities are therefore in principle chemically inert, nonpolar solvents such as aliphatic, aromatic or araliphatic hydrocarbons, for example octane and higher alkanes, toluene, xylenes.

The amount of the tertiary amine (I) to be used in the process of the invention is generally from 5 to 95% by weight, preferably from 20 to 60% by weight, in each case based on the total liquid reaction mixture in the hydrogenation reactor.

The polar solvent (III) to be used in the hydrogenation of carbon dioxide in the process of the invention has an electrostatic factor, also referred to as EF for short, of $\geq 200 \cdot 10^{-30}$ cm and at a pressure of 1013 hPa abs has a boiling point which is at least 5° C. higher than that of formic acid. The polar solvent (III) is to be selected or matched to the tertiary amine (I) so that the polar solvent (III) is present in enriched form in the liquid phase (A). For the present purposes, "in enriched form" means a proportion by weight of >50% of the polar solvent (III) in the liquid phase (A) based on the total amount of polar solvent (III) in the two liquid phases (A) and (B). The proportion by weight is preferably >90%, particularly preferably >95% and very particularly preferably >97%. The polar solvent (III) is generally selected by means of a simple test in which the solubility of the desired polar solvent (III) in the two liquid phases (A) and (B) under the planned process conditions is determined experimentally.

The electrostatic factor EF is defined as the product of the relative dielectric constant $\in_r$ and the dipole moment $\mu$ (see, for example, C. Reichardt, "Solvents and Solvent Effects in Organic Chemistry", 3rd edition, Wiley-VCH Verlag GmbH & Co KGaA, Weinheim 2003, chapter 3.2, page 67 bottom to page 68 top). The abovementioned minimum value of the electrostatic factor ensures that the polar solvent (III) has a certain minimum polarity and the formic acid/amine adduct (II) preferably dissolves therein.

The polar solvent (III) to be used preferably has a boiling point which is at least 10° C. higher, particularly preferably at least 50° C. higher and very particularly preferably at least 85° C. higher, than that of formic acid. A restriction in terms of an upper limit to the boiling point is not necessary since a very low vapor pressure of the polar solvent (III) is in principle an advantage for the process of the invention. In general, the boiling point of the polar solvent (III) at a pressure of 1013 hPa abs, if necessary at a pressure extrapolated by known methods from vacuum to 1013 hPa abs, is below 500° C.

As classes of substances suitable as polar solvents (III), preference is given to diols and also the formic esters thereof, polyols and the formic esters thereof, sulfones, sulfoxides, open-chain or cyclic amides and also mixtures of the classes of substance mentioned.

As suitable diols and polyols, mention may be made by way of example of ethylene glycol (EF=290.3·10$^{-30}$ cm), diethylene glycol (EF=244.0·10$^{-30}$ cm), triethylene glycol, polyethylene glycol, 1,3-propanediol (EF=285.6·10$^{-30}$ cm), 2-methyl-1,3-propanediol, 1,4-butanediol (EF=262.7·10$^{-3}$ cm), dipropylene glycol, 1,5-pentanediol (EF=212.5·10$^{-3}$ cm), 1,6-hexanediol and glycerol. Diols and polyols can, due to their OH groups, be esterified in the presence of formic acid. In the process of the invention, this occurs particularly in the thermal dissociation of the formic acid/amine adduct (II) in the abovementioned distillation unit. Since the formic esters formed display a very similar phase behavior, they are likewise well suited as polar solvent. The water formed in the esterification, which can be an amount of up to 5% by weight based on the total hydrogenation mixture, also does not interfere either in the hydrogenation or in the thermal dissociation. Accumulation of water in continuous operation of the process of the invention does not occur since water in these small amounts can be separated off in the formic acid-high-boiler azeotrope via a side offtake in the distillation unit for thermal dissociation. This may even be advantageous, when using diols or polyols, to add additional water in order to shift the equilibrium between the OH groups and the formic ester groups in the direction of the OH groups. In the case of an addition of water, the amount of water added is generally from 0.1 to 20% by weight based on the total liquid reaction mixture in the hydrogenation reactor.

Suitable sulfoxides are, for example, dialkyl sulfoxides, preferably $C_1$-$C_6$-dialkyl sulfoxides, in particular dimethyl sulfoxide (EF=627.1·10$^{-30}$ cm).

Suitable open-chain or cyclic amides are, for example, formamide (EF=1243.2·10$^{-30}$ cm), N-methylformamide (EF=2352.9·10$^{-3}$ cm), N,N-dimethylformamide (EF=396.5·10$^{-30}$ cm), N-methylpyrrolidone (EF=437.9·10$^{-30}$ cm), acetamide and N-methylcaprolactam.

In the process of the invention, preference is given to using an aliphatic, saturated hydrocarbon having from 2 to 5 OH groups or a formic ester thereof as polar solvent (III). Particularly preferred diols and polyols are ethylene glycol, 1,4-butanediol, 2-methyl-1,3-propanediol and formic esters thereof.

The molar ratio of the polar solvent (III) to be used in the process of the invention to the tertiary amine (I) used is generally from 0.5 to 30 and preferably from 2 to 20.

It is generally known that compounds comprising OH groups accelerate the hydrogenation of carbon dioxide. Thus, for instance, EP 0 095 321 A, EP 0 151 510 A, EP 0 181 078 A, EP 0 357 234 A and DE 44 31 233 A teach the addition of water. In the present process of the invention, too, the use of compounds comprising OH groups as promoter for the hydrogenation of carbon dioxide is preferred in principle. However, since the abovementioned diols and polyols likewise exercise such a positive effect, in the case of these the addition of further compounds comprising OH groups is generally not necessary. On the other hand, when other polar solvents (III) which do not comprise any OH groups are used, for example formic esters, sulfones, sulfoxides or open-chain or cyclic amides, the situation is different. In these cases, it is advantageous to add water and/or alcohols, for example aliphatic, saturated monoalcohols. In general, an addition of from 1 to 500 mmol per mg of the group 8 to 10 metal catalyst is sufficient.

The carbon dioxide to be used in the hydrogenation of carbon dioxide can be used in solid, liquid or gaseous form. It is also possible to use industrially available gas mixtures comprising carbon dioxide as long as these are largely free of carbon monoxide. The hydrogen to be used in the hydrogenation of carbon dioxide is generally gaseous. Carbon dioxide and hydrogen can also comprise inert gases such as nitrogen or noble gases. However, the content of these is advantageously below 10 mol % based on the total amount of carbon dioxide and hydrogen in the hydrogenation reactor. Although larger amounts may likewise be tolerable, they generally require the use of a higher pressure in the reactor which in turn makes further compression energy necessary.

The hydrogenation of carbon dioxide is carried out in the liquid phase at a temperature of from 20 to 200° C. and a total pressure of from 0.2 to 30 MPa abs. The temperature is preferably at least 30° C. and particularly preferably at least 40° C. and also preferably not more than 150° C., particularly preferably not more than 120° C. and very particularly preferably not more than 80° C. The total pressure is preferably at least 1 MPa abs and particularly preferably at least 5 MPa abs and also preferably not more than 20 MPa abs, particularly preferably not more than 15 MPa abs and especially not more than 10 MPa abs.

The partial pressure of carbon dioxide is generally at least 0.5 MPa and preferably at least 2 MPa and also generally not more than 6 MPa and preferably not more than 5 MPa. The partial pressure of hydrogen is generally at least 0.5 MPa and preferably at least 1 MPa and also generally not more than 250 MPa and preferably not more than 10 MPa.

The molar ratio of hydrogen to carbon dioxide in the feed to the hydrogenation reactor is preferably from 0.1 to 10 and particularly preferably from 1 to 3.

The molar ratio of carbon dioxide to tertiary amine (I) in the feed to the hydrogenation reactor is generally from 0.1 to 10 and preferably from 0.5 to 3.

As hydrogenation reactors, it is in principle possible to use all reactors which are suitable in principle for gas/liquid reactions at the given temperature and the given pressure. Suitable standard reactors for liquid-liquid reaction systems are indicated, for example, in K. D. Henkel, "Reactor Types and Their Industrial Applications", in Ullmann's Encyclopedia of Industrial Chemistry, 2005, Wiley-VCH Verlag GmbH & Co. KGaA, DOI: 10.1002/14356007.b04_087, chapter 3.3 "Reactors for gas-liquid reactions". Examples which may be mentioned are stirred tank reactors, tube reactors or bubble column reactors.

The hydrogenation of carbon dioxide in the process of the invention can be carried out batchwise or continuously. In the case of batch operation, the reactor is charged with the desired liquid and if appropriate solid starting materials and auxiliaries and carbon dioxide and hydrogen are subsequently introduced to the desired pressure at the desired temperature. After the reaction is complete, the reactor is generally depressurized and the two liquid phases (A) and (B) which are formed are separated from one another. In the continuous mode of operation, the starting materials and auxiliaries including the carbon dioxide and hydrogen are introduced continuously. However, any heterogeneous fixed-bed catalyst to be used is present beforehand in fixed form in the reactor. Accordingly, the liquid phase is continuously discharged from the reactor so that the average liquid level in the reactor remains constant. Preference is given to the continuous hydrogenation of carbon dioxide.

The average residence time in the reactor is generally from 10 minutes to 5 hours.

The formic acid/amine adduct (II) formed in the hydrogenation of carbon dioxide in the presence of the catalyst to be used and the tertiary amine (I) usually has the general formula (IIa)

$$NR^1R^2R^3 \cdot x\text{HCOOH} \qquad \text{(IIa)}$$

where the radicals $R^1$ to $R^3$ are the radicals described for the tertiary amine (Ia) and x is from 0.5 to 5, preferably from 0.7 to 1.5. The factor x can be determined, for example, by titration with an alcoholic KOH solution against phenolphthalein. The precise composition of the formic acid/amine adduct (II) depends on many parameters, for example the prevailing concentrations of formic acid and tertiary amine (I), pressure, temperature or the presence and nature of further components, in particular a polar solvent (III). The composition of the formic acid/amine adduct (II) can therefore also change over the individual process steps in which the formic acid/amine adduct (II) is in each case referred to in the present patent application. The composition of the formic acid/amine adduct (II) can easily be determined in each process step by determining the formic acid content by acid-base titration and determining the amine content by gas chromatography.

Two liquid phases are formed in the hydrogenation of carbon dioxide by the process of the invention. Liquid phase (A) is enriched with the formic acid/amine adduct (II) and the polar solvent (III). With regard to the formic acid/amine adduct (II), "enriched" means a partition coefficient of the formic acid/amine adduct (II)

$$P = [\text{concentration of formic acid/amine adduct (II) in liquid phase } (A)]/[\text{concentration of formic acid/amine adduct (II) in liquid phase } (B)]$$

of >1. The partition coefficient is preferably $\geq 2$ and particularly preferably $\geq 5$. The liquid phase (B) is enriched with the tertiary amine (I). If a homogeneous catalyst is used, this is likewise present in enriched form in the liquid phase (B).

The two liquid phases (A) and (B) formed are, in the process of the invention, separated from one another and the liquid phase (B) is recirculated to the hydrogenation reactor. Recirculation of a further liquid phase comprising unreacted carbon dioxide present in addition to the two abovementioned liquid phases and also of a gas phase comprising unreacted carbon dioxide and/or unreacted hydrogen to the hydrogenation reactor may also be advantageous. It may also be desirable, for example to discharge undesirable by-products or impurities, to discharge part of the liquid phase (B) and/or part of the carbon dioxide or liquid or gaseous phases comprising carbon dioxide and hydrogen from the process.

The two liquid phases (A) and (B) are generally separated by gravimetric phase separation. This may be carried out using, for example, standard apparatuses and standard methods which are described, for example, in E. Müller et al., "Liquid-Liquid Extraction", in Ullmann's Encyclopedia of Industrial Chemistry, 2005, Wiley-VCH Verlag GmbH & Co. KGaA, D01:10.1002/14356007.b03_06, chapter 3 "Apparatus". In general, the liquid phase (A) enriched with the formic acid/amine adduct (II) and the polar solvent (III) is heavier and forms the lower phase.

The phase separation can be effected, for example, by depressurization, preferably to about or close to atmospheric pressure, and cooling of the liquid reaction mixture, for example to about or close to ambient temperature. However, there is a risk that at least part of the gas dissolved in the liquid phases at the higher reaction pressure, in particular carbon dioxide, will degas during the depressurization and have to be compressed separately as a gas stream and recirculated to the hydrogenation reactor. Likewise, the liquid phase (B) also has to be compressed separately before recirculation to the hydrogenation reactor. Each of the two compressor stages for the gas and liquid phases to be recirculated requires a suitable compressor designed appropriately for the pressure difference to be overcome and consumes additional energy in operation.

In the context of the present invention, it has surprisingly been found that in the case of the present system, i.e. a liquid phase (A) enriched with the formic acid/amine adduct (II) and the polar solvent (III) and a liquid phase (B) enriched with the tertiary amine (I) and in the case of the use of a homogeneous catalyst also with this, the two liquid phases separate very well from one another even at a significantly elevated pressure. The separation of the one liquid phase (A) enriched with the formic acid/amine adduct (II) and the polar solvent (III) from the other liquid phase (B) enriched with the tertiary amine (I) and the recirculation of the liquid phase (B) to the hydrogenation reactor are therefore preferably carried out at a pressure of from 1 to 30 MPa abs in the process of the invention. Depending on the total pressure in the hydrogenation reactor, the pressure is preferably not more than 15 MPa abs and particularly preferably not more than 10 MPa abs. It is even possible to separate the two liquid phases from one another without prior depressurization and recirculate the liquid phase (B) to the hydrogenation reactor without an appreciable pressure increase. In this case, and also in the case of an only slight depressurization, it is possible to entirely dispense with recirculation of any gas phase. Whether this omission is possible for the respective specific system should be determined beforehand in the case of doubt by simple experimental examples.

The phase separation is particularly preferably carried out at a pressure of at least 50%, very particularly preferably at least 90% and in particular at least 95%, of the reaction pressure. The pressure in the phase separation is particularly preferably not more than 105% and very particularly preferably not more than 100% of the reaction pressure.

It has surprisingly also been found that in the case of the present system the two liquid phases separate very readily from one another even at an elevated temperature corresponding to the reaction temperature. In this case, no cooling is necessary for the phase separation and no subsequent heating of the liquid phase (B) to be recirculated is required, which likewise saves energy.

Established experience with phase separation under elevated pressure and at elevated temperature is surpassed by the liquid phase (B) of the system according to the invention having a particularly high absorption capacity for carbon dioxide under superatmospheric pressure. This means that any excess carbon dioxide which has not reacted in the hydrogenation reaction is highly preferentially present in the liquid phase (B) and can thus be recirculated without problems as liquid to the reactor.

The formic acid/amine adduct (II) in the liquid phase (A) which has been separated off is then thermally dissociated into free formic acid and free tertiary amine (I) in a distillation unit, with the free formic acid formed being removed by distillation and the free tertiary amine (I) present in the bottoms from the distillation unit and also the polar solvent (III) being recirculated to the hydrogenation reactor. The formic acid liberated can be taken off, for example, (i) at the top, (ii) at the top and as side offtake stream or (iii) only as side offtake stream. If formic acid is taken off at the top, a formic acid purity of up to 99.9% by weight is possible. When formic acid is taken off as side offtake stream, aqueous formic acid is obtained, with a mixture comprising about 85% by weight of formic acid being of particular importance here in industrial practice. Depending on the water content of the feed to the distillation unit, the majority of the formic acid is taken off as overhead product or as side product. If necessary, it is even possible to take off formic acid only as side product, in which case the required amount of water may be deliberately added. The thermal dissociation of the formic acid/amine adduct (II) is generally carried out under the process parameters known from the prior art in respect of pressure, temperature and configuration of the apparatus. Thus, for example, reference may be made to the descriptions in EP 0 181 078 A or WO 2006/021,411. The distillation unit to be used generally comprises a distillation column which generally comprises random packing elements, ordered packings and/or bubble cap trays.

The bottom product taken off from the distillation unit can still comprise small residual amounts of formic acid, but the molar ratio of formic acid to tertiary amine (I) is preferably $\geq 0.1$ and particularly preferably $\geq 0.05$.

In general, the temperature at the bottom of the distillation column is at least 130° C., preferably at least 150° C. and particularly preferably at least 170° C., and generally not more than 210° C., preferably not more than 190° C. and particularly preferably not more than 185° C. The pressure is generally at least 1 hPa abs, preferably at least 50 hPa abs and particularly preferably at least 100 hPa abs, and generally not more than 500 hPa abs, preferably not more than 300 hPa abs and particularly preferably not more than 250 hPa abs.

If appropriate, a water-comprising stream of formic acid is taken off as side product. In the case of addition of water, for example to promote the hydrogenation, this is even particularly advantageous.

DE 34 28 319 A has described the thermal dissociation of an adduct of formic acid and a tertiary amine having $C_6$-$C_{14}$-alkyl radicals in a dissociation column. Likewise, WO 2006/021,411 also describes the thermal dissociation of an adduct of formic acid and a tertiary amine having a boiling point at atmospheric pressure of from 105 to 175° C. in a dissociation column. EP 0 563 831 A similarly discloses the thermal dissociation of an adduct of formic acid and a tertiary amine having a boiling point higher than that of formic acid, with added formamide being said to give a particularly color-stable formic acid.

FIG. 1 shows a schematic block diagram of a possible embodiment of the process of the invention. Here, the individual letters have the following meanings:
A=hydrogenation reactor
B=phase separator
C=distillation unit Carbon dioxide and hydrogen are fed into the hydrogenation reactor "A". In this reactor, the carbon dioxide and hydrogen are reacted in the presence of a catalyst comprising an element of group 8, 9 or 10 of the Periodic Table, a tertiary amine (I) and a polar solvent (III) to form a formic acid/amine adduct (II). The two liquid phases (A) and (B) are formed. Liquid phase (A) is enriched with the formic acid/amine adduct (II) and the polar solvent (III), while liquid phase (B) is enriched with the tertiary amine (I) and in the case of the use of a homogeneous catalyst also with the latter. The two liquid phases are fed to a phase separator "B" and separated from one another. Liquid phase (B), which is generally the upper phase, is recirculated to the hydrogenation reactor "A". Liquid phase (A) is fed to a distillation unit "C" and the formic acid/amine adduct (II) formed in the hydrogenation reactor "A" is thermally dissociated therein into free formic acid and tertiary amine (I). The free formic acid is, for example, removed as overhead product. The bottoms from the distillation unit "C" are recirculated to the hydrogenation reactor "A".

It is of course possible to supplement the process of the invention by further process steps or inflows or outflows of streams if required. A nonlimiting example which may be mentioned is, for instance, the introduction of auxiliaries such as tertiary amine (I), polar solvent (III), homogeneous catalyst or water to maintain their concentrations in the process.

Figure 2:
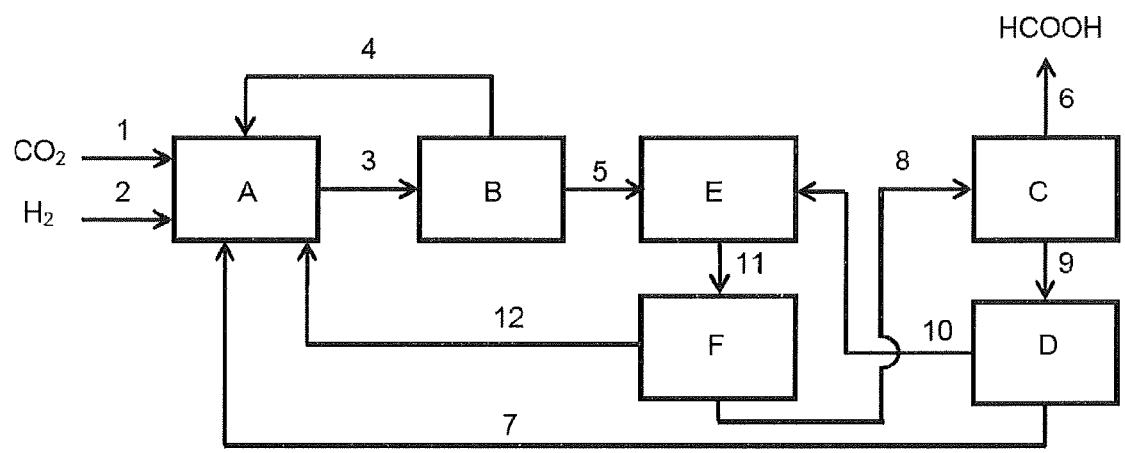
FIG. 2 depicts a schematic block diagram of a preferred embodiment of the process of the invention.

FIG. 2 shows a schematic block diagram of a preferred embodiment of the process of the invention. Here, the individual letters have the following meanings:
A=hydrogenation reactor
B=phase separator
C=distillation column
D=phase separator
E=extraction apparatus
F=phase separator As regards the carrying out of the process in the apparatuses "A" and "B", what has been said in respect of FIG. 1 applies. In the preferred process as per FIG. 2, the liquid phase (B), which is generally the upper phase, is also recirculated to the hydrogenation reactor "A". However, in this case the liquid phase (A) is firstly subjected to an extraction with tertiary amine (I) to be recirculated in order to separate off further homogeneous catalyst before being fed to the distillation column "C". This extraction is carried out in the extraction apparatus "E" with subsequent phase separation in the phase separator "F". In the latter, the two liquid phases (C) and (D) separate. The liquid phase (C), which is the amine phase enriched in the homogeneous catalyst and generally represents the upper phase, is fed to the hydrogenation reactor "A". The liquid phase (D) which is enriched with the formic acid/amine adduct (II) and the polar solvent (III) is fed to the distillation column "C" and the formic acid/amine adduct (II) is thermally dissociated therein into free formic acid and tertiary amine (I). The free formic acid is, for example, removed as overhead product. The bottoms from the distillation column "C" are separated in the phase separator "D" into two liquid phases (E) and (F). The liquid phase (E), which comprises mainly the tertiary amine (I) and generally represents the upper phase, is fed to the extraction apparatus "E". The liquid phase (F), which comprises mainly the polar solvent (III), is recirculated to the hydrogenation reactor "A".

The process of the invention makes it possible to obtain concentrated formic acid in high yield and high purity by hydrogenation of carbon dioxide. In particular, it provides a particularly simple and elegant mode of operation which compared to the prior art has a simpler process concept, simpler process stages, a smaller number of process stages and simpler apparatuses. Thus, for example, if the tertiary amine (I) and the polar solvent are appropriately selected in the case of the use of a homogeneous catalyst, the latter is separated off from the formic acid/amine adduct (II) by phase separation and recirculated without further work-up steps to the hydrogenation reactor. The prompt separation of the catalyst from the formic acid/amine adduct (II) formed suppresses a backreaction with decomposition into carbon dioxide and hydrogen. In addition, losses of catalyst and thus losses of noble metal are minimized by the retention or removal of the catalyst as a result of the formation of two liquid phases. Furthermore, no complicated separate base replacement is required in the process of the invention, so that the formic acid/amine adduct (II) formed in the hydrogenation reactor can be used directly for the thermal dissociation. The tertiary amine (I) liberated here is recirculated to the hydrogenation reactor. This phase separation can even be carried out under superatmospheric pressure. The simpler process concept makes it possible for the production plant required for carrying out the process of the invention to be made more compact in the sense of a smaller space requirement and the use of fewer apparatuses compared to the prior art. It has a lower capital cost requirement and a lower energy consumption.

Further removal of the catalyst by means of the tertiary amine (I) to be recirculated can be effected by additional extraction of the stream comprising formic acid/amine adduct (II) before it is fed to the thermal dissociation. Owing to the resulting still lower content of homogeneous catalyst in the formic acid/amine adduct (II) to be dissociated, a possible backreaction in the dissociation with decomposition into carbon dioxide and hydrogen is suppressed even better. In addition, further introduction of homogeneous catalyst in the form of fresh catalyst is reduced further by the resulting increased recirculation factor of the homogeneous catalyst.

EXAMPLES

Unless indicated otherwise, the trialkylamines mentioned are in each case the corresponding tri-n-alkylamines.

Examples A-1 to A-27

Hydrogenation and Phase Separation

Unless indicated otherwise, a 250 ml autoclave made of Hastelloy C and provided with a magnetic stirrer bar was charged under inert conditions with tertiary amine, polar solvent and homogeneous catalyst to give, a two-phase mixture (upper phase: amine and catalyst; lower phase: solvent). The autoclave was subsequently closed and $CO_2$ was injected at room temperature. $H_2$ was then injected and the reactor was heated while stirring (700 rpm). After the desired reaction time, the autoclave was cooled and the reaction mixture was depressurized. Unless indicated otherwise, a two-phase product mixture was obtained, with the upper phase being enriched with the still free tertiary amine and the homogeneous catalyst and the lower phase being enriched with the polar solvent and the formic acid/amine adduct formed. In some examples, the partition coefficient K of ruthenium $K$=[Ru concentration in the upper phase]/[Ru concentration in the lower phase]

was determined by means of atomic adsorption spectrometry (AAS). The total content of formic acid in the formic acid/amine adduct was determined by titration with 0.1 N KOH in 2-propanol against phenolphthalein with subtraction of the blank. The TON, the TOF and the reaction rate were calculated therefrom. The parameters and results of the individual experiments are shown in tables 1.1 to 1.7.

The blank results from small amounts of carbon dioxide also dissolving in the phase comprising formic acid/amine adduct and being able to be titrated by KOH against phenolphthalein. The blank was determined separately for each example by means of a fully analogous blank experiment in which only the homogeneous catalyst was omitted and the emulsified total sample was titrated as described above at the end.

Examples A-1 to A-27 show that high to very high reaction rates of even up to above 1 mol kg$^{-1}$ h$^{-1}$ can be achieved in the process of the invention even with variation of the tertiary amine, the polar solvent, the catalyst in respect of the ligands and the metal component, the amount of catalyst and also with additional addition of water. All systems examined formed two phases, with the upper phase in each case being enriched with the still free tertiary amine and the homogeneous catalyst and the lower phase in each case being enriched with the polar solvent and the formic acid/amine adduct formed.

Examples B-1 to B-12

Phase Behavior and $CO_2$ Solubility under Pressure

In these examples, the phase behavior of mixtures comprising tertiary amine, polar solvent and formic acid/amine adduct in respect of the specific solubility of $CO_2$ under superatmospheric pressure was examined. For this purpose, 0.5 g of formic acid was in each case added to a two-phase mixture comprising 10.0 g of polar solvent and 10.0 g of tertiary amine while stirring vigorously. The formic acid in each case reacted with the tertiary amine to form the corresponding formic acid/amine adduct which in each case dissolved in the phase of the polar solvent. 4 ml of the emulsion obtained in each case were introduced into a high-pressure sight cell and separation into two phases was awaited. The volume levels of the two liquid phases were subsequently marked and $CO_2$ was injected to 6.5 MPa abs at 20° C. Further $CO_2$ was in each case introduced until a constant pressure of 6.5 MPa abs was established. The volume levels of the two liquid phases were marked again after 15 minutes and compared with the original levels before injection of the $CO_2$. An increase in the phase volume is attributable to dissolution of $CO_2$. The parameters and results of the individual experiments are shown in tables 2.1 to 2.3.

The examples firstly show that the two phases are retained in many systems even at high pressure and phase separation is thus still possible without problems even at 6.5 MPa abs. Secondly, the volume increase of the upper liquid phase (B) enriched with the tertiary amine in the examples shows that many of the tertiary amines tested have a high $CO_2$ absorption capacity.

In the preferred embodiment of phase separation and recirculation of the liquid phase (B) to the hydrogenation reactor under superatmospheric pressure, this is particularly advantageous since the $CO_2$ can be recirculated in dissolved form. In addition, a high $CO_2$ solubility in the liquid phase (B) is particularly advantageous for the hydrogenation when a homogeneous catalyst is used, since the homogeneous catalyst is present in the liquid phase (B) and a high concentration of dissolved $CO_2$ is thus present as starting material in its environment.

Examples C-1 to C-34

Distribution of the Homogeneous Catalysts

In these examples, the distribution of various homogeneous catalysts in various two-phase mixtures comprising an upper phase comprising free tertiary amine and a lower phase comprising polar solvent and formic acid/amine adduct was examined. In experiments C-1 to C-26, 5 g of the formic acid-trihexylamine adduct (prepared from formic acid and trihexylamine in a molar ratio of amine to formic acid of 1:2) were in each case dissolved in 5 g of the polar solvent at room temperature while stirring and admixed with 5 g of trihexylamine and 10 mg of the homogeneous Ru catalyst. The two-phase system obtained was stirred vigorously at room temperature for 30 minutes. In experiments C-27 to C-34, 2.5 g of formic acid were in each case mixed with 20 g of the respective amine and stirred at room temperature for 30 minutes. After the reaction, 5 g of the lower phase were separated off or, in the case of single-phase mixtures, the reaction mixture was used and added to a mixture of 10 mg of [Ru(Pn Bu$_3$)$_4$(H)$_2$], 5 g of the respective amine and 5 g of ethylene glycol were added and the two-phase system obtained was stirred vigorously at room temperature for 10 minutes. After separation of the two phases in experiments C-1 to C-34, the partition coefficient K of ruthenium K=[Ru concentration in the upper phase]/[Ru concentration in the lower phase]

was subsequently determined by means of atomic adsorption spectrometry (AAS).

The parameters and results of the individual experiments are shown in Tables 3.1 to 3.2.

The examples show that the partition coefficient K of ruthenium was significantly above 1 in all systems tested, in some systems even significantly above 10. The various homogeneous Ru catalysts were enriched in the upper, amine-containing phase in all systems tested (various polar solvents, various tertiary amines).

Examples D-1 to D-2

Hydrogenation, Phase Separation, Extraction and Catalyst Recirculation

Figure 3:
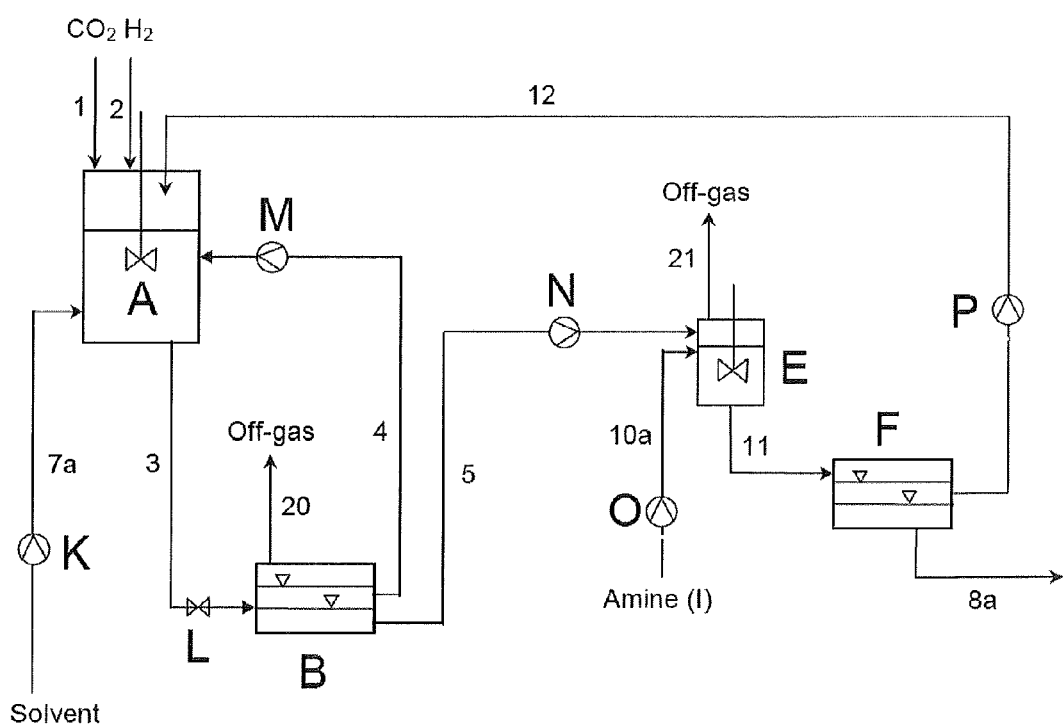
FIG. 3 depicts a laboratory plant used to examine the continuous hydrogenation, phase separation, extraction and catalyst recirculation.

To examine the continuous hydrogenation, phase separation, extraction and catalyst recirculation, a laboratory plant as shown in FIG. 3 was used. Here, the individual letters have the following meanings:
A=hydrogenation reactor (270 ml autoclave made of Hastelloy C with blade stirrer)
B=phase separator
E=extraction vessel (350 ml stirred glass vessel with glass blade stirrer)
F=phase separator
K=solvent pump
L=depressurization valve
M=recirculation pump for tertiary amine (I) and homogeneous catalyst
N=product stream pump
O=amine pump
P=recirculation pump for tertiary amine (I) and extracted homogeneous catalyst
Furthermore:
Solvent=solvent
Off-gas=off-gas
Amine (I)=tertiary amine (I)

Under inert conditions, an emulsion was produced by dissolving the homogeneous catalyst in tertiary amine (I) and subsequently adding the polar solvent while stirring. The parameters of the individual experiments are shown in Tables 4.1 and 4.2. The hydrogenation reactor "A" and the phase separator "B" were then charged with the emulsion produced. The extraction vessel "E" and the phase separator "F" were charged with a mixture of tertiary amine (I) and polar solvent. The hydrogenation reactor "A" was then heated while stirring and, after setting an initial H$_2$ pressure, CO$_2$ was injected. Further H$_2$ was subsequently injected and the hydrogenation reactor "A" was then left under the conditions set with depressurization valve "L" closed for the stated initial reaction time. The depressurization valve "L" was subsequently opened and the plant was operated continuously. Here, polar solvent as stream 7a, CO$_2$ as stream 1 and H$_2$ as stream 2 were fed in continuously. Product mixture went via the opened depressurization valve "L" into the phase separator "B" and was separated into two phases. The upper phase was recirculated as stream 4 to the hydrogenation reactor "A". The lower phase was conveyed as stream 5 to the extraction vessel "E". In this, fresh tertiary amine (I) was introduced as stream 10a for extraction of the residual homogeneous catalyst. The tertiary amine (I) was in each case introduced in an amount corresponding to the amount discharged via stream 8a. In the subsequent phase separator "F", the output from the extraction vessel "E" was separated into two phases. The upper phase was recirculated as stream 12 to the hydrogenation reactor "A". The lower phase was discharged as stream 8a. Gas which accumulated in the phase separator "B" and extraction vessel "E" was removed as off-gas. The amount of formic acid formed was determined in stream 8a by titration with 0.1 N KOH in 2-propanol against Phenolphthalein. The TON, the TOF and the reaction rate were calculated therefrom. The ruthenium contents were determined by means of atomic adsorption spectrometry (AAS). Under these conditions, the plant was in each case operated for a number of hours. The results of the individual experiments are likewise shown in Table 4.2.

Examples D-1 and D-2 show that very good removal of the homogeneous catalyst with subsequent recirculation to the hydrogenation reactor is also possible via the phase separation when the plant is operated continuously. Thus, the upper phase to be recirculated from the phase separator "B" in each case comprised, with 175 ppm by weight (D-1) or 390 ppm by weight (D-2), very significant enrichment of the homogeneous catalyst compared to only 15 ppm by weight (D-1) or 26 ppm by weight (D-2) in the lower phase (product stream). The preferred extraction using tertiary amine (I) in the extraction vessel "E" with subsequent phase separation in the phase separator "F" enabled the product stream to be depleted further in homogeneous catalyst, in example D-1 from 15 ppm by weight to 10 ppm by weight and in example D-2 from 26 ppm by weight to 11 ppm by weight, which corresponds to a further depletion to 67% and 42%, respectively. The upper phase in the phase separator "F" comprised 46 ppm by weight (D-1) or 160 ppm by weight (D-2), which could in each case be recirculated to the hydrogenation reactor. It is thus possible to separate off a higher proportion of the homogeneous catalyst directly and reuse it in the hydrogenation.

TABLE 1.1

|  | Example A-1 | Example A-2 | Example A-3 | Example A-4 |
|---|---|---|---|---|
| Tertiary amine | 49 g of trihexylamine | 50 g of trihexylamine | 30 g of trihexylamine | 50 g of trihexylamine |
| Polar solvent | 20 g of 1,4-butanediol | 25 g of ethylene glycol diformate 25 g of ethylene glycol | 70 g of 2-methyl-1,3-propanediol | 50 g of 2-methyl-1,3-propanediol 5.0 g of C$_{17}$-alkanol mixture |
| Catalyst | 0.1 g of [Ru(P"Bu$_3$)$_4$(H)$_2$] | 0.1 g of [Ru(P"Bu$_3$)$_4$(H)$_2$] | 0.1 g of [Ru(P"Bu$_3$)$_4$(H)$_2$] | 0.1 g of [Ru(P"Bu$_3$)$_4$(H)$_2$] |

TABLE 1.1-continued

|  | Example A-1 | Example A-2 | Example A-3 | Example A-4 |
| --- | --- | --- | --- | --- |
| Peculiarity | Double flushing with 1 MPa abs of $H_2$ | — | — | — |
| Injection of $CO_2$ | 14.4 g to 2.9 MPa abs | 17.6 g to 2.7 MPa abs | 15.8 g to 2.6 MPa abs | 15.7 g to 3.0 MPa abs |
| Injection of $H_2$ | To 8.9 MPa abs | To 9.0 MPa abs | To 8.7 MPa abs | To 9.1 MPa abs |
| Heating | To 50° C. | To 50° C. | To 50° C. | To 50° C. |
| Pressure change | To 9.4 MPa abs | To 9.9 MPa abs | To 8.7 MPa abs | To 9.0 MPa abs |
| Reaction time | 5 hours | 1 hour | 1 hour | 1 hour |
| Peculiarity | — | — | — | $C_{17}$-Alkanol mixture was present in the amine/catalyst phase |
| Partition coefficient K of ruthenium | 28.8 | not determined | not determined | not determined |
| TON | 321 | 150 | 727 | 539 |
| TOF | 64 $h^{-1}$ | 150 $h^{-1}$ | 727 $h^{-1}$ | 539 $h^{-1}$ |
| Reaction rate | 0.06 mol $kg^{-1}$ $h^{-1}$ | 0.17 mol $kg^{-1}$ $h^{-1}$ | 0.90 mol $kg^{-1}$ $h^{-1}$ | 0.60 mol $kg^{-1}$ $h^{-1}$ |

TABLE 1.2

|  | Example A-5 | Example A-6 | Example A-7 | Example A-8 |
| --- | --- | --- | --- | --- |
| Tertiary amine | 50 g of trihexylamine | 50 g of trihexylamine | 30 g of trihexylamine | 50 g of trihexylamine |
| Polar solvent | 50 g of 2-methyl-1,3-propanediol | 50 g of 2-methyl-1,3-propanediol | 70 g of 2-methyl-1,3-propanediol | 50 g of ethylene glycol diformate 5.0 g of 2-octyldodecanol |
| Catalyst | 0.1 g of $[Ru(P^nBu_3)_4(H)_2]$ | 0.4 g of $[Ru(P^nBu_3)_4(H)_2]$ | 0.4 g of $[Ru(P^nBu_3)_4(H)_2]$ 0.2 g of $P^nBu_3$ | 0.1 g of $[Ru(P^nBu_3)_4(H)_2]$ |
| Peculiarity | — | — | Addition of 1.0 g of water | — |
| Injection of $CO_2$ | 14.0 g to 2.8 MPa abs | 16.2 g to 2.9 MPa abs | 20.1 g to 3.8 MPa abs | 14.3 g to 2.6 MPa abs |
| Injection of $H_2$ | To 10.8 MPa abs | To 7.1 MPa abs | To 8.1 MPa abs | To 7.3 MPa abs |
| Heating | To 50° C. | To 50° C. | To 50° C. | To 50° C. |
| Pressure change | To 11.3 MPa abs | To 8.2 MPa abs | To 8.9 MPa abs | To 8.4 MPa abs |
| Reaction time | 1 hour | 1 hour | 1 hour | 1 hour |
| Peculiarity | — | — | — | — |
| Partition coefficient K of ruthenium | not determined | not determined | not determined | not determined |
| TON | 304 | 171 | 166 | 157 |
| TOF | 304 $h^{-1}$ | 171 $h^{-1}$ | 166 $h^{-1}$ | 157 $h^{-1}$ |
| Reaction rate | 0.38 mol $kg^{-1}$ $h^{-1}$ | 0.83 mol $kg^{-1}$ $h^{-1}$ | 0.75 mol $kg^{-1}$ $h^{-1}$ | 0.17 mol $kg^{-1}$ $h^{-1}$ |

TABLE 1.3

|  | Example A-9 | Example A-10 | Example A-11 | Example A-12 |
| --- | --- | --- | --- | --- |
| Tertiary amine | 50 g of trihexylamine | 50 g of trihexylamine | 50 g of N,N-dimethyldecylamine | 50 g of tributylamine |
| Polar solvent | 50 g of ethylene glycol | 50 g of 2-methyl-1,3-propanediol | 50 g of ethylene glycol | 50 g of 2-methyl-1,3-propanediol |
| Catalyst | 0.1 g of $[Ru(P^nBu_3)_4(H)_2]$ | 0.1 g of $[Ru(P^nBu_3)_4(H)_2]$ | 0.1 g of $[Ru(P^nBu_3)_4(H)_2]$ | 0.2 g of $[Ru(P^nBu_3)_4(H)_2]$ |
| Peculiarity | — | Addition of 1.0 g of water | — | — |
| Injection of $CO_2$ | 16.8 g to 3.3 MPa abs | 16.0 g to 3.1 MPa abs | 13.3 g to 2.2 MPa abs | 18.2 g to 2.9 MPa abs |
| Injection of $H_2$ | To 8.1 MPa abs | To 8.1 MPa abs | To 7.2 MPa abs | To 7.9 MPa abs |
| Heating | To 50° C. | To 50° C. | To 50° C. | To 50° C. |
| Pressure change | To 7.5 MPa abs | To 8.0 MPa abs | To 8.5 MPa abs | To 8.3 MPa abs |
| Reaction time | 1 hour | 1 hour | 1 hour | 1 hour |
| Peculiarity | — | — | — | — |
| Partition coefficient K of ruthenium | 225 | not determined | not determined | not determined |
| TON | 374 | 444 | 271 | 199 |
| TOF | 374 $h^{-1}$ | 444 $h^{-1}$ | 271 $h^{-1}$ | 199 $h^{-1}$ |
| Reaction rate | 0.44 mol $kg^{-1}$ $h^{-1}$ | 0.56 mol $kg^{-1}$ $h^{-1}$ | 0.31 mol $kg^{-1}$ $h^{-1}$ | 0.52 mol $kg^{-1}$ $h^{-1}$ |

TABLE 1.4

|  | Example A-13 | Example A-14 | Example A-15 | Example A-16 |
| --- | --- | --- | --- | --- |
| Tertiary amine | 50 g of N-methyl-dicyclohexylamine | 50 g of trioctylamine | 50 g of tripropylamine | 50 g of N,N-dimethyl-cyclohexylamine |
| Polar solvent | 50 g of 2-methyl-1,3-propanediol | 50 g of 2-methyl-1,3-propanediol | 50 g of 2-methyl-1,3-propanediol | 50 g of ethylene glycol |

TABLE 1.4-continued

|  | Example A-13 | Example A-14 | Example A-15 | Example A-16 |
| --- | --- | --- | --- | --- |
| Catalyst | 0.1 g of [Ru(P"Bu$_3$)$_4$(H)$_2$] | 0.2 g of [Ru(P"Bu$_3$)$_4$(H)$_2$] | 0.2 g of [Ru(P"Bu$_3$)$_4$(H)$_2$] | 0.1 g of [Ru(P"Bu$_3$)$_4$(H)$_2$] |
| Peculiarity | — | — | — | — |
| Injection of $CO_2$ | 15.0 g to 3.1 MPa abs | 15.7 g to 3.2 MPa abs | 15.0 g to 2.0 MPa abs | 15.0 g to 2.3 MPa abs |
| Injection of $H_2$ | To 8.1 MPa abs | To 8.2 MPa abs | To 7.1 MPa abs | To 8.1 MPa abs |
| Heating | To 50° C. | To 50° C. | To 50° C. | To 50° C. |
| Pressure change | To 7.30 MPa abs | To 8.8 MPa abs | To 7.3 MPa abs | To 8.2 MPa abs |
| Reaction time | 1 hour | 1 hour | 1 hour | 1 hour |
| Peculiarity | — | — | — | — |
| Partition coefficient K of ruthenium | not determined | not determined | not determined | not determined |
| TON | 404 | 171 | 162 | 325 |
| TOF | 404 h$^{-1}$ | 171 h$^{-1}$ | 162 h$^{-1}$ | 325 h$^{-1}$ |
| Reaction rate | 0.49 mol kg$^{-1}$ h$^{-1}$ | 0.41 mol kg$^{-1}$ h$^{-1}$ | 0.38 mol kg$^{-1}$ h$^{-1}$ | 0.42 mol kg$^{-1}$ h$^{-1}$ |

TABLE 1.5

|  | Example A-17 | Example A-18 | Example A-19 | Example A-20 |
| --- | --- | --- | --- | --- |
| Tertiary amine | 50 g of tributylamine | 50 g of N-methyl-dicyclohexylamine | 50 g of trihexylamine | 50 g of trihexylamine |
| Polar solvent | 50 g of 1,4-butanediol | 50 g of 1,4-butanediol | 50 g of 2-methyl-1,3-propanediol | 50 g of 2-methyl-1,3-propanediol |
| Catalyst | 0.2 g of [Ru(P"Bu$_3$)$_4$(H)$_2$] | 0.2 g of [Ru(P"Bu$_3$)$_4$(H)$_2$] | 0.15 g of [Rh(PPh$_3$)$_4$(H)] | 0.3 g of [Ru(P"octyl$_3$)$_4$(H)$_2$] |
| Peculiarity | — | — | — | — |
| Injection of $CO_2$ | 15.8 g to 2.7 MPa abs | 14.9 g to 2.9 MPa abs | 15.8 g to 2.9 MPa abs | 15.9 g to 3.3 MPa abs |
| Injection of $H_2$ | To 7.7 MPa abs | To 7.9 MPa abs | To 7.9 MPa abs | To 9.3 MPa abs |
| Heating | To 50° C. | To 50° C. | To 50° C. | To 50° C. |
| Pressure change | To 8.0 MPa abs | To 7.8 MPa abs | To 8.6 MPa abs | To 9.5 MPa abs |
| Reaction time | 1 hour | 1 hour | 5 hours | 1 hour |
| Peculiarity | — | — | — | — |
| Partition coefficient K of ruthenium | not determined | not determined | not determined | not determined |
| TON | 55 | 250 | 38 | 150 |
| TOF | 55 h$^{-1}$ | 250 h$^{-1}$ | 7.6 h$^{-1}$ | 150 h$^{-1}$ |
| Reaction rate | 0.16 mol kg$^{-1}$ h$^{-1}$ | 0.58 mol kg$^{-1}$ h$^{-1}$ | 0.05 mol kg$^{-1}$ h$^{-1}$ | 0.29 mol kg$^{-1}$ h$^{-1}$ |

TABLE 1.6

|  | Example A-21 | Example A-22 | Example A-23 | Example A-24 |
| --- | --- | --- | --- | --- |
| Tertiary amine | 50 g of trihexylamine | 50 g of trihexylamine | 50 g of trihexylamine | 50 g of trihexylamine |
| Polar solvent | 50 g of 2-methyl-1,3-propanediol 3.0 g of C$_{17}$-alkanol mixture | 50 g of 2-methyl-1,3-propanediol 3.0 g of C$_{17}$-alkanol mixture | 50 g of 2-methyl-1,3-propanediol 2.0 g of 2-ethylhexanoic acid | 50 g of 2-methyl-1,3-propanediol |
| Catalyst | 0.1 g of [Ru(P"Bu$_3$)$_4$(H)$_2$] | 0.1 g of [Ru(P"Bu$_3$)$_4$(H)$_2$] 0.09 g of bis(dicyclohexyl)-phosphinoethane | 0.1 g of [Ru(P"Bu$_3$)$_4$(H)$_2$] 0.09 g of bis(dicyclohexyl)-phosphinoethane | 0.1 g of [Ru(PPh$_3$)$_3$(Cl)(OAc)] 0.08 g of P"Bu$_3$ |
| Peculiarity | — | — | — | — |
| Injection of $CO_2$ | 14.7 g to 2.9 MPa abs | 15.0 g to 3.0 MPa abs | 15.4 g to 2.8 MPa abs | 15.2 g to 3.0 MPa abs |
| Injection of $H_2$ | To 10.9 MPa abs | To 11.0 MPa abs | To 10.8 MPa abs | To 8.0 MPa abs |
| Heating | To 50° C. | To 50° C. | To 50° C. | To 50° C. |
| Pressure change | To 11.6 MPa abs | To 11.4 MPa abs | To 11.6 MPa abs | To 8.3 MPa abs |
| Reaction time | 1 hour | 1 hour | 1 hour | 1 hour |
| Peculiarity | C$_{17}$-alkanol mixture was present in the amine/catalyst phase | C$_{17}$-alkanol mixture was present in the amine/catalyst phase | 2-ethylhexanoic acid was present in the amine/catalyst phase | — |
| Partition coefficient K of ruthenium | 4.8 | 3.0 | 4.8 | 5.7 |
| TON | 497 | 956 | 838 | 353 |
| TOF | 497 h$^{-1}$ | 956 h$^{-1}$ | 838 h$^{-1}$ | 353 h$^{-1}$ |
| Reaction rate | 0.55 mol kg$^{-1}$ h$^{-1}$ | 1.08 mol kg$^{-1}$ h$^{-1}$ | 0.93 mol kg$^{-1}$ h$^{-1}$ | 0.36 mol kg$^{-1}$ h$^{-1}$ |

TABLE 1.7

|  | Example A-25 | Example A-26 | Example A-27 |
|---|---|---|---|
| Tertiary amine | 50 g of N-methyl-dicyclohexylamine | 50 g of tributylamine | 25 g of trihexylamine |
| Polar solvent | 50 g of 2-methyl-1,3-propanediol | 50 g of 2-methyl-1,3-propanediol | 25 g of 2-methyl-1,3-propanediol |
| Catalyst | 0.1 g of $[Ru(P''Bu_3)_4(H)_2]$ | 0.1 g of $[Ru(P''Bu_3)_4(H)_2]$ 0.09 g of bis(dicyclohexyl)-phosphinoethane | 0.05 g of $[Ru(P''Bu_3)_4(H)_2]$ 0.042 g of bis(dicyclohexyl)-phosphinoethane |
| Peculiarity | — | — | 100 ml autoclave with blade stirrer |
| Injection of $CO_2$ | 15.8 g to 3.7 MPa abs | 15.9 g to 2.65 MPa abs | 7.9 g to 2.6 MPa abs |
| Injection of $H_2$ | To 8.7 MPa abs | To 7.7 MPa abs | To 8.1 MPa abs |
| Heating | To 50° C. | To 50° C. | To 50° C. |
| Pressure change | To 7.6 MPa abs | To 8.0 MPa abs | not determined |
| Reaction time | 1 hour | 1 hour | 1 hour |
| Peculiarity | — | — | — |
| Partition coefficient K of ruthenium | 15.3 | 10.6 | 5.6 |
| TON | 841 | 792 | 430 |
| TOF | 841 $h^{-1}$ | 792 $h^{-1}$ | 430 $h^{-1}$ |
| Reaction rate | 0.97 mol $kg^{-1}$ $h^{-1}$ | 0.85 mol $kg^{-1}$ $h^{-1}$ | 0.56 mol $kg^{-1}$ $h^{-1}$ |

TABLE 2.1

|  | Example B-1 | Example B-2 | Example B-3 | Example B-4 |
|---|---|---|---|---|
| Tertiary amine | trioctylamine | trihexylamine | tripentylamine | N-methyldicyclohexylamine |
| Polar solvent | 2-methyl-1,3-propanediol | 2-methyl-1,3-propanediol | 2-methyl-1,3-propanediol | 2-methyl-1,3-propanediol |
| Number of liquid phases before injection of $CO_2$ | Two | Two | Two | Two |
| Behavior of the amine-comprising liquid phase (B) | Volume increase (dissolution of $CO_2$) | Volume increase (dissolution of $CO_2$) | Amine phase mostly dissolves in the $CO_2$ phase | Volume increase (dissolution of $CO_2$) |
| Behavior of the liquid phase (A) comprising solvent and adduct | No visible change | No visible change | No visible change | No visible change |
| Peculiarity | — | — | — | — |

TABLE 2.2

|  | Example B-5 | Example B-6 | Example B-7 | Example B-8 |
|---|---|---|---|---|
| Tertiary amine | trihexylamine | N,N-dimethyldecyl-amine | N,N-dimethylcyclo-hexylamine | N,N-dioctylmethylamine |
| Polar solvent | 1,4-butanediol | 1,4-butanediol | 1,4-butanediol | 2-methyl-1,3-propanediol |
| Number of liquid phases before injection of $CO_2$ | Two | Two | Two | Two |
| Behavior of the amine-comprising liquid phase (B) | Volume increase (dissolution of $CO_2$) | Volume increase (dissolution of $CO_2$) | Volume increase (dissolution of $CO_2$) | Volume increase (dissolution of $CO_2$) |
| Behavior of the liquid phase (A) comprising solvent and adduct | No visible change | No visible change | No visible change | No visible change |
| Peculiarity | — | — | — | — |

TABLE 2.3

|  | Example B-9 | Example B-10 | Example B-11 | Example B-12 |
|---|---|---|---|---|
| Tertiary amine | N,N-dimethylnonyl-amine | N-ethyldiisopropyl-amine | tris(2-ethylhexyl)amine | N-ethyldiisopropylamine |
| Polar solvent | 2-methyl-1,3-propanediol | 1,4-bButanediol | 1,4-butanediol | 2-methyl-1,3-propanediol |
| Number of liquid phases before injection of $CO_2$ | Two | Two | Two | Two |

TABLE 2.3-continued

|  | Example B-9 | Example B-10 | Example B-11 | Example B-12 |
|---|---|---|---|---|
| Behavior of the amine-comprising liquid phase (B) | Volume increase (dissolution of $CO_2$) | Volume increase (dissolution of $CO_2$) | Amine phase mostly dissolves in the $CO_2$ phase | Volume increase (dissolution of $CO_2$) |
| Behavior of the liquid phase (A) comprising solvent and adduct | No visible change | No visible change | No visible change | No visible change |
| Peculiarity | — | — | — | — |

TABLE 3.1

| Example | Tertiary Amine | Polar solvent | Factor x in the formic acid/amine adduct amine •xHCOOH used | Catalyst | Partition coefficient K of ruthenium |
|---|---|---|---|---|---|
| C-1 | trihexylamine | sulfolane | 2.0 | $[Ru(P^nBu_3)_4(H)_2]$ | 7.8 |
| C-2 | trihexylamine | sulfolane | 2.0 | $[Ru(P^nOctyl_3)_4(H)_2]$ | 35 |
| C-3 | trihexylamine | dimethyl sulfoxide (DMSO) | 2.0 | $[Ru(P^nBu_3)_4(H)_2]$ | 3.4 |
| C-4 | trihexylamine | dimethyl sulfoxide (DMSO) | 2.0 | $[Ru(P^nOctyl_3)_4(H)_2]$ | 25.7 |
| C-5 | trihexylamine | dimethylformamide | 2.0 | $[Ru(P^nBu_3)_4(H)_2]$ | 6.2 |
| C-6 | trihexylamine | dimethylformamide | 2.0 | $[Ru(P^nOctyl_3)_4(H)_2]$ | 4.0 |
| C-7 | trihexylamine | ethylene glycol | 2.0 | $[Ru(P^nBu_3)_4(H)_2]$ | 16.3 |
| C-8 | trihexylamine | ethylene glycol | 2.0 | $[Ru(P^nOctyl_3)_4(H)_2]$ | 31.3 |
| C-9 | trihexylamine | 1,3-propanediol | 2.0 | $[Ru(P^nBu_3)_4(H)_2]$ | 8.9 |
| C-10 | trihexylamine | 1,3-propanediol | 2.0 | $[Ru(P^nOctyl_3)_4(H)_2]$ | 2.3 |
| C-11 | trihexylamine | 1,4-butanediol | 2.0 | $[Ru(P^nBu_3)_4(H)_2]$ | 18.5 |
| C-12 | trihexylamine | 1,4-butanediol | 2.0 | $[Ru(P^nOctyl_3)_4(H)_2]$ | 43.3 |
| C-13 | trihexylamine | diethylene glycol | 2.0 | $[Ru(P^nBu_3)_4(H)_2]$ | 16.0 |
| C-14 | trihexylamine | diethylene glycol | 2.0 | $[Ru(P^nOctyl_3)_4(H)_2]$ | 26.7 |
| C-15 | trihexylamine | 1,5-pentanediol | 2.0 | $[Ru(P^nBu_3)_4(H)_2]$ | 4.3 |
| C-16 | trihexylamine | 1,5-pentanediol | 2.0 | $[Ru(P^nOctyl_3)_4(H)_2]$ | 19.4 |
| C-17 | trihexylamine | dipropylene glycol | 2.0 | $[Ru(P^nBu_3)_4(H)_2]$ | 4.6 |
| C-18 | trihexylamine | dipropylene glycol | 2.0 | $[Ru(P^nOctyl_3)_4(H)_2]$ | 2.6 |
| C-19 | trihexylamine | 2-methyl-1,3-propanediol | 2.0 | $[Ru(P^nBu_3)_4(H)_2]$ | 20.0 |
| C-20 | trihexylamine | 2-methyl-1,3-propanediol | 2.0 | $[Ru(P^nOctyl_3)_4(H)_2]$ | 24.0 |

TABLE 3.2

| Example | Tertiary Amine | Polar solvent | Factor x in the formic acid/amine adduct amine •xHCOOH | Catalyst | Partition coefficient K of ruthenium |
|---|---|---|---|---|---|
| C-21 | trihexylamine | ethylene glycol diformate | 2.0 | $[Ru(P^nBu_3)_4(H)_2]$ | 28.1 |
| C-22 | trihexylamine | ethylene glycol diformate | 2.0 | $[Ru(P^nOctyl_3)_4(H)_2]$ | 42.5 |
| C-23 | trihexylamine | 1,4-butylene glycol diformate | 2.0 | $[Ru(P^nBu_3)_4(H)_2]$ | 3.8 |
| C-24 | trihexylamine | 1,4-butylene glycol diformate | 2.0 | $[Ru(P^nOctyl_3)_4(H)_2]$ | 10.8 |
| C-25 | trihexylamine | 2-methyl-1,3-propylene glycol diformate | 2.0 | $[Ru(P^nBu_3)_4(H)_2]$ | 4.7 |
| C-26 | trihexylamine | 2-methyl-1,3-propylene glycol diformate | 2.0 | $[Ru(P^nOctyl_3)_4(H)_2]$ | 8.5 |
| C-27 | N,N-dimethyldecylamine | ethylene glycol | not determined | $[Ru(P^nBu_3)_4(H)_2]$ | 8.9 |
| C-28 | trioctylamine | ethylene glycol | not determined | $[Ru(P^nBu_3)_4(H)_2]$ | 1.5 |
| C-29 | tripentylamine | ethylene glycol | not determined | $[Ru(P^nBu_3)_4(H)_2]$ | 9.5 |
| C-30 | N-methyl-dicyclohexylamine | ethylene glycol | not determined | $[Ru(P^nBu_3)_4(H)_2]$ | 18.7 |
| C-31 | N,N-dimethyl-cyclohexylamine | ethylene glycol | not determined | $[Ru(P^nBu_3)_4(H)_2]$ | 20.4 |
| C-32 | N-ethyldiisopropylamine | ethylene glycol | not determined | $[Ru(P^nBu_3)_4(H)_2]$ | 27.0 |
| C-33 | tripropylamine | ethylene glycol | not determined | $[Ru(P^nBu_3)_4(H)_2]$ | 50.0 |
| C-34 | tributylamine | ethylene glycol | not determined | $[Ru(P^nBu_3)_4(H)_2]$ | 160 |

TABLE 4.1

|  |  | Example E-1 | Example E-2 |
|---|---|---|---|
| Emulsion for hydrogenation reactor "A" and phase separator "B" | Tertiary amine | 73 g of trihexylamine | 73 g of trihexylamine |
|  | Polar solvent | 93 g of 2-methyl-1,3-propanediol | 93 g of 2-methyl-1,3-propanediol |
|  | Catalyst | 0.37 g of [Ru(P"Bu$_3$)$_4$(H)$_2$] 0.34 g of bis(dicyclohexyl)-phosphinoethane | 0.74 g of [Ru(P"Bu$_3$)$_4$(H)$_2$] 0.34 g of P"Bu$_3$ |
| Mixture for extraction vessel "E" and phase separator "F" | Tertiary amine | 50% by weight of trihexylamine | 33% by weight of trihexylamine |
|  | Polar solvent | 50% by weight of 2-methyl-1,3-propanediol | 67% by weight of 2-methyl-1,3-propanediol |
| Start-up | Heating | with stirring (1000 rpm) to 50° C. | with stirring (1300 rpm) to 50° C. |
|  | Initial H$_2$ pressure | 3.0 MPa abs | 3.6 MPa abs |
|  | Injection of CO$_2$ | 12.0 g of CO$_2$ to 7.4 MPa abs | 13.0 g of CO$_2$ to 7.4 MPa abs |
|  | Injection of H$_2$ | To 8.1 MPa abs | To 8.9 MPa abs |
|  | Initial reaction time | 1 hour | 1 hour |

TABLE 4.2

|  |  | Example E-1 | Example E-2 |
|---|---|---|---|
| Continuous operation | CO$_2$ | 21.8 g/h | 13.0 g/h |
|  | H$_2$ | 2.7 g/h | 2.7 g/h |
|  | Polar solvent | 83 g/h | 43 g/h |
|  | Hydrogenation reactor "A" | 50° C., 8.0 MPa abs | 50° C., 8.8 MPa abs |
|  | Phase separator "B" | 50° C., 0.1 MPa abs | 50° C., 0.1 MPa abs |
|  | Extraction vessel "E" | 20° C., 0.1 MPa abs | 20° C., 0.1 MPa abs |
|  | Phase separator "F" | 20° C., 0.1 MPa abs | 20° C., 0.1 MPa abs |
| Formic acid | TON | 744 | 194 |
|  | TOF | 149 h$^{-1}$ | 56 h$^{-1}$ |
|  | Reaction rate | 0.43 mol kg$^{-1}$ h$^{-1}$ | 0.32 mol kg$^{-1}$ h$^{-1}$ |
| Ruthenium contents | Lower phase in phase separator "B" | 15 ppm by weight | 26 ppm by weight |
|  | Upper phase in phase separator "B" | 175 ppm by weight | 390 ppm by weight |
|  | Lower phase in phase separator "F" | 10 ppm by weight | 11 ppm by weight |
|  | Upper phase in phase separator "F" | 46 ppm by weight | 160 ppm by weight |

The invention claimed is:

1. A process for preparing formic acid by hydrogenation of carbon dioxide in the presence of a homogenous catalyst comprising an element of group 8, 9 or 10 of the Periodic Table, a tertiary amine (I) and a polar solvent (III) at a pressure of from 0.2 to 30 MPa abs and a temperature of from 20 to 200° C. to form two liquid phases, separation of the one liquid phase (A) enriched with the formic acid/amine adduct (II) from the other liquid phase (B) enriched with the homogenous catalyst together with the tertiary amine (I), and recirculation of the liquid phase (B) to the hydrogenation reactor, wherein (a) an amine which at a pressure of 1013 hPa abs has a boiling point which is at least 5° C. higher than that of formic acid and is present in enriched form in the liquid phase (B) is used as tertiary amine (I);

(b) a solvent whose electrostatic factor is $\geq 200 \cdot 10^{-30}$ Cm and which at a pressure of 1013 hPa abs has a boiling point which is at least 5° C. higher than that of formic acid and is present in enriched form in the liquid phase (A) is used as polar solvent (III);

(c) the formic acid/amine adduct (II) of the liquid phase (A) which has been separated off is thermally dissociated into free formic acid and free tertiary amine (I) in a distillation unit;

(d) the free formic acid is removed by distillation; and (e) the free tertiary amine (I) comprised in the bottoms from the distillation unit and the polar solvent (III) are recirculated to the hydrogenation reactor.

2. The process according to claim 1, wherein a homogenous catalyst comprising ruthenium is used.

3. The process according to claim 1, wherein a metal-organic complex comprising an element of group 8, 9 or 10 of the Periodic Table and at least one phosphine group having at least one unbranched or branched, acyclic or cyclic, aliphatic radical having from 1 to 12 carbon atoms, where individual carbon atoms can also be substituted by >P—, is used as homogeneous catalyst.

4. The process according to claim 1, wherein, in feature (e), the bottoms from the distillation unit are separated into a phase comprising the free tertiary amine (I) and a phase comprising the polar solvent (III) and the two phases are recirculated separately to the hydrogenation reactor, with the phase comprising the free tertiary amine (I) being recirculated via an extraction unit to the hydrogenation reactor and homogeneous catalyst being extracted in the said extraction unit from the liquid phase (A) which has been separated off before the formic acid/amine adduct (II) in the liquid phase (A) which had been separated off is, according to feature (c) thermally dissociated in a distillation unit into free formic acid and free tertiary amine (I).

5. The process according to claim 1, wherein an amine of the general formula (Ia)

where the radicals $R^1$ to $R^3$ are identical or different and are each, independently of one another, an unbranched or branched, acyclic or cyclic, aliphatic, araliphatic or aromatic radical having in each case from 1 to 16 carbon atoms, where individual carbon atoms can also be substituted, independently of one another, by a hetero group selected from the group consisting of —O— and >N— or two or all three radicals can also be joined to one another to form a chain comprising at least four atoms in each case, is used as tertiary amine (I).

6. The process according to claim 5, wherein an amine of the general formula (Ia) in which the radicals $R^1$ to $R^3$ are selected independently from the group consisting of $C_1$-$C_{12}$-alkyl, $C_5$-$C_8$-cycloalkyl, benzyl and phenyl is used as tertiary amine (I).

7. The process according to claim 5, wherein a saturated amine of the general formula (Ia) is used as tertiary amine (I).

8. The process according to claim 7, wherein an amine of the general formula (Ia) in which the radicals $R^1$ to $R^3$ are selected independently from the group consisting of $C_5$-$C_8$-alkyl is used as tertiary amine (I).

9. The process according to claim 1, wherein an aliphatic, saturated hydrocarbon having from 2 to 5 OH groups or a formic ester thereof is used as polar solvent (III).

10. The process according to claim 1, wherein the hydrogenation is carried out at a molar ratio of carbon dioxide to tertiary amine (I) of from 0.1 to 10.

11. The process according to claim 1, wherein the separation of the one liquid phase (A) enriched with the formic acid/amine adduct (II) and the polar solvent (III) from the other liquid phase (B) enriched with the homogenous catalyst together with the tertiary amine (I) and the recirculation of the liquid phase (B) to the hydrogenation reactor are carried out at a pressure of from 1 to 30 MPa abs.

* * * * *